United States Patent
Nakahira et al.

(10) Patent No.: US 8,585,599 B2
(45) Date of Patent: Nov. 19, 2013

(54) ULTRASONOGRAPHIC DEVICE AND METHOD FOR IMPROVING ULTRASONOGRAPHIC DEVICE IMAGE QUALITY

(75) Inventors: Kenji Nakahira, Fujisawa (JP); Atsushi Miyamoto, Yokohama (JP)

(73) Assignee: Hitachi Medical Corporation, Tokyo (JP)

( * ) Notice: Subject to any disclaimer, the term of this patent is extended or adjusted under 35 U.S.C. 154(b) by 694 days.

(21) Appl. No.: 12/599,056

(22) PCT Filed: May 9, 2008

(86) PCT No.: PCT/JP2008/058639
§ 371 (c)(1),
(2), (4) Date: Jul. 7, 2010

(87) PCT Pub. No.: WO2008/140043
PCT Pub. Date: Nov. 20, 2008

(65) Prior Publication Data
US 2010/0280378 A1 Nov. 4, 2010

(30) Foreign Application Priority Data
May 9, 2007 (JP) .................................. 2007-124519

(51) Int. Cl.
*A61B 8/00* (2006.01)
(52) U.S. Cl.
USPC ............ 600/443; 600/407; 600/437; 382/128
(58) Field of Classification Search
USPC .................................. 600/437, 443; 382/128
See application file for complete search history.

(56) References Cited

U.S. PATENT DOCUMENTS

| 5,497,777 A | 3/1996 | Abdel-Malek et al. |
| 2008/0112637 A1 | 5/2008 | Horie |
| 2012/0035478 A1* | 2/2012 | Nishihara et al. ............. 600/443 |
| 2012/0189179 A1* | 7/2012 | Gering et al. ................. 382/128 |

FOREIGN PATENT DOCUMENTS

| JP | 2005-296331 | 10/2005 |
| JP | 2006-116307 | 5/2006 |
| JP | 2007-026334 | 2/2007 |

OTHER PUBLICATIONS

J.L. Starck, E.J. Candes, et al; IEEE Trans. Image Processing 11, 6, pp. 670-684 (2002) "The Curvelet Transform for Image Denoising", Jun. 6, 2002.

(Continued)

*Primary Examiner* — Unsu Jung
*Assistant Examiner* — Amanda Lauritzen
(74) *Attorney, Agent, or Firm* — Antonelli, Terry, Stout & Kraus, LLP.

(57) ABSTRACT

It is possible to improve an image quality of an ultrasonographic device and improve visibility of a tissue structure and a lesion. According to a noise amount estimated for each of at least two resolution levels and reliability of the noise amount estimation, a corrected noise amount is calculated. An intensity conversion is performed on a decomposition coefficient obtained by a multi-resolution decomposition process using the corrected noise amount. Moreover, by performing intensity conversion of the respective decomposition coefficients according to a plurality of decomposition coefficients, it is possible to generate a high-quality image. Furthermore, by switching processing parameters in accordance with the imaging condition, the image type, and the imaging object, it is possible to simultaneously realize the processing time and the image quality appropriate for the purpose.

8 Claims, 16 Drawing Sheets

(56) References Cited

OTHER PUBLICATIONS

M.N. Do, M. Vetterli: IEEE Trans. Image Processing, 14, 12, pp. 2091-2106, "The Contourlet Transform: An Efficient Directional Multiresolution Image Representation", 2005.

N. G. Kingsbury; Proceedings of European Signal Processing conference, pp. 319-322, "The Dual-Tree Complex Wavelet Transform: A New Efficient Tool for Image Restoration and Enhancement", 1998.

E.P. Simoncelli, W.T. Freeman: Proceedings of IEEE International Conference on Image Processing, 3, pp. 444-447; The Steerable Pyramid: A Flexible Architecture for Multi-Scale Derivative Computation, Oct. 1995.

E.H.O. Ng: Applied Science in Electrical and Computer Engineering, University of Waterloo (Master thesis), pp. 1-112 Speckle Noise Reduction Via Homomorphic Elliptical Threshold Rotations in the Complex Wavelet Domain, 2005.

S. Gupta et al., "A versatile technique for visual enhancement of medical ultrasound images", vo. 17, No. 3, Apr. 13, 2007.

Aleksandra Pizurica et al., "A review of wavelet denoising in MRI and ultrasound brain imaging", vol. 2, No. 2, May 1, 2006.

European Search Report for Application No. 08752522.6—2218 / 2151193 PCT/JP2008058639, issued on Aug. 6, 2012.

* cited by examiner

FIG. 8(a)
FIG. 8(b)
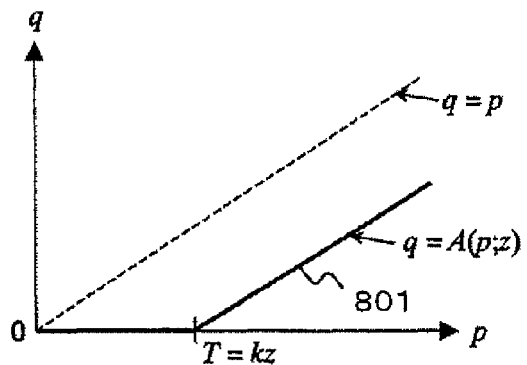
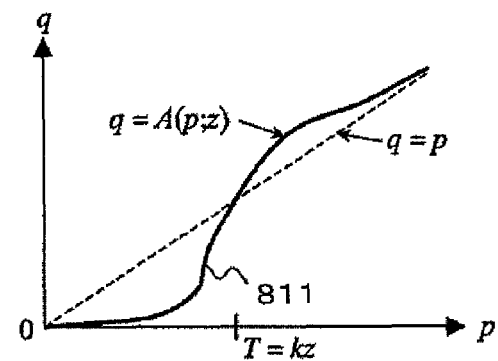
FIG. 9
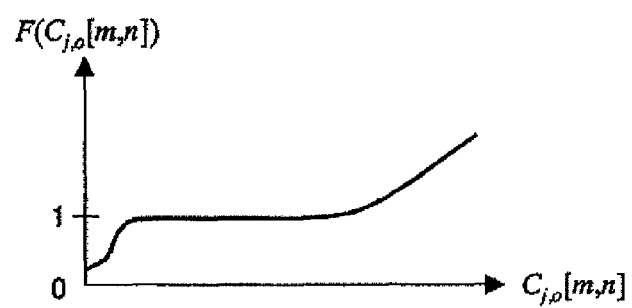

FIG. 12(a)    FIG. 12(b)
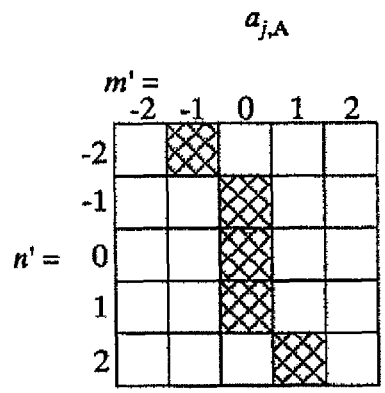
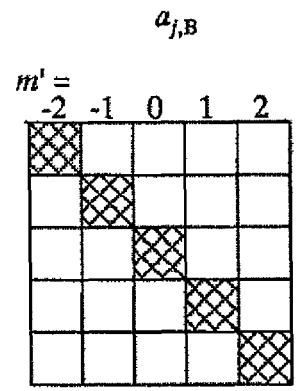
EDGE DIRECTION
FIG. 13
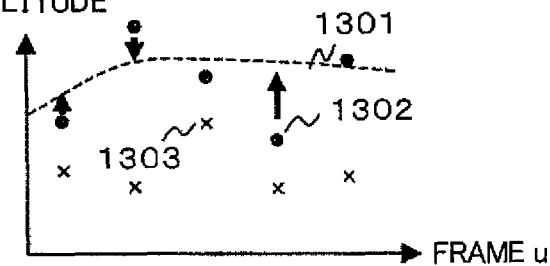

FIG. 17

| IMAGING CONDITION | | IMAGE TYPE | IMAGE OBJECT | PROCESSING PARAMETERS | | |
|---|---|---|---|---|---|---|
| ULTRASOUND PROBE | ... | | | DECOMPOSE MULTIPLEX RESOLUTION PROCESSING | | ... |
| | | | | RESOLUTION LEVEL | EDGE DIRECTION | |
| CONVEX | ... | B MODE | ABDOMEN | 5 | 6,6,6,6,6 | ... |
| CONVEX | ... | DOPPLER | ABDOMEN | 5 | 6,6,6,4,4 | ... |
| CONVEX | ... | (AS DESIRED) | ABDOMEN | 4 | 6,6,4,4 | ... |
| SECTOR | ... | B MODE | HEART | 4 | 4,4,4,4 | ... |
| ... | ... | ... | ... | ... | ... | ... |
| (AS DESIRED) | ... | (AS DESIRED) | (AS DESIRED) | 5 | 4,4,4,4 | ... |

1701 PROCESSING PARAMETERS
1702 IMAGING CONDITION
1703 IMAGE TYPE
1704 IMAGE OBJECT
1705 DECOMPOSE MULTIPLEX RESOLUTION PROCESSING
1706

ULTRASONOGRAPHIC DEVICE AND METHOD FOR IMPROVING ULTRASONOGRAPHIC DEVICE IMAGE QUALITY

BACKGROUND OF THE INVENTION

The present invention relates to an ultrasonographic device which obtains images by transmitting and receiving ultrasounds to and from a subject, and more particularly to an ultrasonographic device provided with a function to subject the obtained image to image improvement processing by image processing and a method for improving the image quality of the ultrasonographic device.

Ultrasonographic devices are used in examining various regions within the body including the abdomen and the heart. Ultrasonographic devices, having many advantages including the absence of harm to living bodies unlike X-ray examining devices, handling ease and capability of permitting moving image observation on a real time basis, are extensively utilized. An ultrasonographic device irradiates ultrasounds from an ultrasound probe toward a subject, receives reflected waves from tissues within the subject with the ultrasound probe, and displays the received information on a monitor. By scanning multiple parts with ultrasounds focused in a specific direction, a two-dimensional image can be obtained on a real time basis. The types of ultrasound images include B mode images obtained by converting the reflectance of a tissue of a living subject into the brightness of pixel values, Doppler images having information on the moving velocity of the living body tissue, tissue elastographs having hue information according to the distortion quantity or elasticity of the living body tissue, and synthetic images obtained by synthesizing information contained in these images.

However, a two-dimensional image obtained by the ultrasonographic device contains speckle noise generated by the interference of multiple reflected waves from fine structures within the living body. Further more, as received signals obtained with the ultrasound probe are bandwidth-limited signals, high frequency components which should otherwise be obtained on the tissue boundary may fail to be sufficiently obtained, and invite blurring of edges contained in the image. These phenomena including the occurrence of speckle noise and the blurring of edges give rise to quality deterioration of the image, which would adversely affect diagnosis. In order to accurately read and image important structures of morbid regions among others, it is required to display ultrasound images reduced in speckle noise and so processed as to sharpen edges.

Techniques for reducing speckle noise include frequency compounding and spatial compounding. Frequency compounding is a technique by which multiple images are generated by irradiating ultrasounds differing in frequency toward the same region and a single image by summing and averaging those images.

As the pattern of speckle noise substantially varies with the frequency of the ultrasounds used and, on the other hand the reflected waves from the tissue boundary or elsewhere are less subject to variations with the frequency, speckle noise can be reduced by the summing and averaging. However, since the frequency is used in a divided way in frequency compounding, there is a problem that the frequency band of the image is narrowed and edges are blurred. On the other hand, spatial compounding is a technique by which multiple images are generated by irradiating the same region with ultrasounds in different directions and a single image is obtained by summing and averaging those images. According to this technique, speckle noise is reduced by utilizing the variation of the pattern of speckle noise with the irradiating direction of ultrasounds. However, as obtaining a single image takes a long time by spatial compounding, there is a problem of a drop in image displaying velocity.

On the other hand, as a method different from those referred to above, there is a noise reducing technique using image processing. The advancement of performance enhancement and cost reduction of image processors in recent years has made it relatively ease to mount on hardware complex image processing, whose practical application previously was difficult in respect of processing speed. Long established noise reducing techniques, such as the one using a smoothing filter, are known to involve problems of edge blurring and loss of vital signals, and noise removing techniques using multiple resolution analysis, typically wavelet transform and Laplacian pyramid transform, and edge sharpening techniques (for instance Patent Documents 1 through 3).

More recently, as more sophisticated multiple resolution analyzing systems, Curvelet transform (Non-Patent Document 1), Contourlet transform (Non-Patent Document 2), complex Wavelet transform (Non-Patent Document 3) and steerable pyramid transform (Non-Patent Document 4) have been proposed.

Furthermore, the application of these sophisticated multi-level resolving systems to ultrasonographic devices is also proposed in Non-Patent Document 5.

In the conventional Wavelet transform, the edge direction is divided into three, and in the Laplacian pyramid transform, the edge direction is only one, the sophisticated multi-level resolving systems allow the edge direction to be divided into four or more. In the context, the edge direction is divided into K means resolution at each resolution level and in each position into K resolution coefficients vividly reacting to a pattern having brightness variations in K types of mutually different directions. Whereas an image is expressed in resolution coefficients in three edge directions including vertical (0°), transverse (90°) and oblique (45° and 135°) in the conventional Wavelet transform, in this transform an edge in the 45° direction and another in the 135° direction cannot be distinguished from each other. In order to accomplish higher performance in image quality improvement, it is essential to use a multi-level resolving system whose edge direction is divided into at least four.

According to the image quality improving technique based on a multi-level resolution, the intensities of resolution coefficients are converted on the basis of the estimated amount of noise usually contained in each resolution coefficient. Thus, by reconstructing the image, after conserving or emphasizing the intensities of resolution coefficients estimated to contain large amounts of signal components and, conversely, reducing the intensities of resolution coefficients estimated to contain large amounts of noise components, from the resolution coefficients, an image reduced in noise and having sharpened edges can be obtained. Therefore, the estimation if the noise amount and the intensity conversion of the resolution coefficients are processing steps of vital importance.

Patent Document 1: U.S. Pat. No. 5,497,777
Patent Document 2: Japanese Patent Application Laid-Open Publication No. 2006-116307
Patent Document 3: Japanese Patent Application Laid-Open Publication No. 2005-296331
Non-Patent Document 1: J. L. Starck, E. J. Candes, et al.: IEEE Trans. Image Processing 11, 6, pp. 670-684 (2002)
Non-Patent Document 2: M. N. Do, M. Vetterli: IEEE Trans. Image Processing, 14, 12, PP. 2091-2106 (2005)

Non-Patent Document 3: N. G. Kingsbury: Proceedings of European Signal Processing Conference, pp. 319-322 (1998)

Non-Patent Document 4: E. P. Simoncelli, W. T. Freeman: Proceedings of IEEE International Conference on Image Processing, 3, PP. 444-447 (1995)

Non-Patent Document 5: E. H. O. Ng: Applied science in electrical and computer engineering, University of Waterloo (Master thesis), pp. 1-112 (2005)

BRIEF SUMMARY OF THE INVENTION

However, there are some cases in which image quality improving techniques proposed in Non-Patent Documents 1 through 5 cannot achieve sufficient improving effects on low S/N images, typically including ultrasound images living bodies, as enumerated below. The present invention is intended to provide sufficiently high performance in the improvement of image quality even in such cases.

(1) The amount of speckle noise in ultrasound image, by its nature, depends on imaging conditions (including the type and magnification of the ultrasound probe, the frequency used, the presence or absence of compounding, and the scanning pitch), the type of the image (B mode image, Doppler image, tissue elastograph, synthetic image or the like) and the imaging object, and varies with the resolution level, edge direction and position. Furthermore, at a resolution level or in an edge direction or a position where signal components are greater relative to noise components, signals and noise are sometimes difficult to distinguish from each other. This results in a problem that steady estimation of the noise amount against these differences in imaging conditions, image type and imaging object is difficult. According to some known techniques, for instance, noise estimation is carried out on the basis of the assumption that resolution coefficients dominated by noise components constitute a majority, but this assumption does not always holds true.

(2) It is usually difficult to distinguish noise components and signal components from each other. Where the S/N ratio is comparatively high, the amplitude is often great for resolution coefficients in which signal components are dominant, and therefore sufficiently high performance of distinction can be achieved even if information regarding the amplitudes of individual resolution coefficients alone is used as proposed in Patent Document 1. However, for low S/N images, it is difficult to distinguish noise and signals according to information regarding individual resolution coefficients alone, and how to achieve sufficient distinguishing performance even in such case poses a challenge to be met.

(3) The processing time taken to improve image quality and the performance level of image quality improvement are usually in a trade-off relationship with each other. Meanwhile, the required processing time differs with the purpose of examination; for instance, where observation of fast acting tissues of the heart, for instance, is wanted in moving pictures at a high frame rate, processing involving a smaller amount of calculation is required. However, in simple processing involving no large amount of calculation, no sufficient performance can be achieved where, for instance, a region whose variations over time are slow is desired to be examined in detail.

The problems noted in (1) through (3) above lead to failures in intensity conversion of resolution coefficients and in achieving sufficient improvement of image quality.

The present invention addresses the problems by an image quality improving method for ultrasound images including the following steps of processing and an ultrasonographic device mounted with the image quality improving method.

(1) In order to estimate the noise amount with high precision, the estimated value of the noise amount is figured for each resolution level. However, since some of the noise amounts may be poor in the precision of estimation as referred to above, reliability of noise amounts, it is characterized in that high-precision corrected values of the estimated noise amounts are figured out by assigning a level of reliability to each estimated noise amount and correcting the estimated noise amount according to the level of reliability. The levels of reliability can, for instance, be made ready in advance as constants within the system or be given as the distance between the estimated value of a noise amount calculated by a method different from the noise amount estimation method and the foregoing estimated noise amount.

(2) For distinguishing noise components and signal components from each other, not only information on individual resolution coefficients with respect to each position, resolution level and edge direction but also information on the distribution of resolution coefficients obtained from multiple resolution coefficients is utilized. The tissue shape, regularity or some other factor of signal components sometimes causes resolution coefficients to manifest a characteristic distribution. For instance, in the vicinities of the peak of a distribution of resolution coefficients, resolution coefficients of a similarly high amplitude are more likely to be present ("in the vicinities of certain resolution coefficients" means a set of position, resolution level and edge direction, and includes the resolution coefficient in question). It is possible to improve the distinguishing performance by capturing the information on resolution coefficient distribution referred to above as a characteristic amount and determining noise components and signal components on the basis of this characteristic amount. Further, for moving images, information on image frames in a continuous time series is utilized. Since signal components are more regular and slower in variation over time than noise components, improvement in distinguishing performance can be realized by extracting regular characteristics in corresponding positions in image frames in the time series.

(3) Characteristically, processing parameters are so set as to enable appropriate image displaying speed and image quality effect according the imaging conditions, the type of the image and the imaging object to be obtained. For instance, processing parameters are set as to provide the highest possible performance in image quality improvement for an image displaying speed determined by the imaging conditions, the type of the image and the imaging object without sacrificing the displaying speed. Processing parameters relevant to the trade-off between image quality and processing time include, for instance, the number of resolution level divisions and that of edge directions in multi-level resolution, whether or not it is done for each resolution level, each edge direction and each position of the object of noise amount estimation, the number of resolution coefficients to be used for distinction between noise components and signal components of each resolution coefficient, and whether or not information on image frames in a time series is utilized.

One of the specific advantages of varying the processing parameters is that, for instance, the frequency range in which signals and noise can be distinguished from each other is lowered, which means greater effectiveness in a large amount of noise components is involved at relatively low frequencies, with an increase in the number of resolution level divisions in multi-level resolution. Also, the tissue shape can be conserved more accurately and complex tissue shape that can be examined more in detail with an increase in the number of edge direction divisions in multi-level resolution. Further, even higher performance can be achieved by making available multiple algorithms in the multi-level resolving system, noise amount estimation system, noise amount correction system and system for distinguishing noise components and signal components from each other and switching over among these algorithms.

According to the invention, it is made possible to obtain ultrasound images reduced in noise content by using in ultrasonographic devices and in image quality improving methods for ultrasonographic devices a multi-level resolution method, estimating and correcting the noise amounts by using resolution coefficients of multiple resolution levels, and converting the intensities of resolution coefficients based on the multiple resolution coefficients and corrected noise amounts, and thereby to enable the visibility of tissue structure and morbid regions to be improved over earlier devices.

Furthermore, it is made possible to achieve both a reduction in processing time according to the purpose of use and improve image quality by switching over processing parameters according to the imaging conditions, the type of the image and the imaging object.

BRIEF DESCRIPTION OF THE DRAWINGS

FIGS. 8(a), 8(b) illustrate the amplitude conversion of resolution coefficients.

FIG. 9 illustrates correction of resolution coefficients based on the conservation degree.

FIGS. 12(a), 12(b) illustrate intensity conversion based on weighted summing of multiple resolution coefficients in nearby positions.

FIG. 13 illustrates intensity conversion of resolution coefficients based on resolution coefficients in multiple nearby frames.

FIG. 17 shows a table listing processing parameters matching different imaging conditions, types of image and imaging objects.

DETAILED DESCRIPTION OF THE INVENTION

Exemplary modes for carrying out the present invention will be described below with reference to accompanying drawings.

The invention relates to processing and a device performing image processing that utilizes multi-level resolution to improve the image quality of picked-up images by transmitting and receiving ultrasounds.

Exemplary embodiments of the invention will be described with reference to FIG. 1 through FIG. 15.

Figure 1:
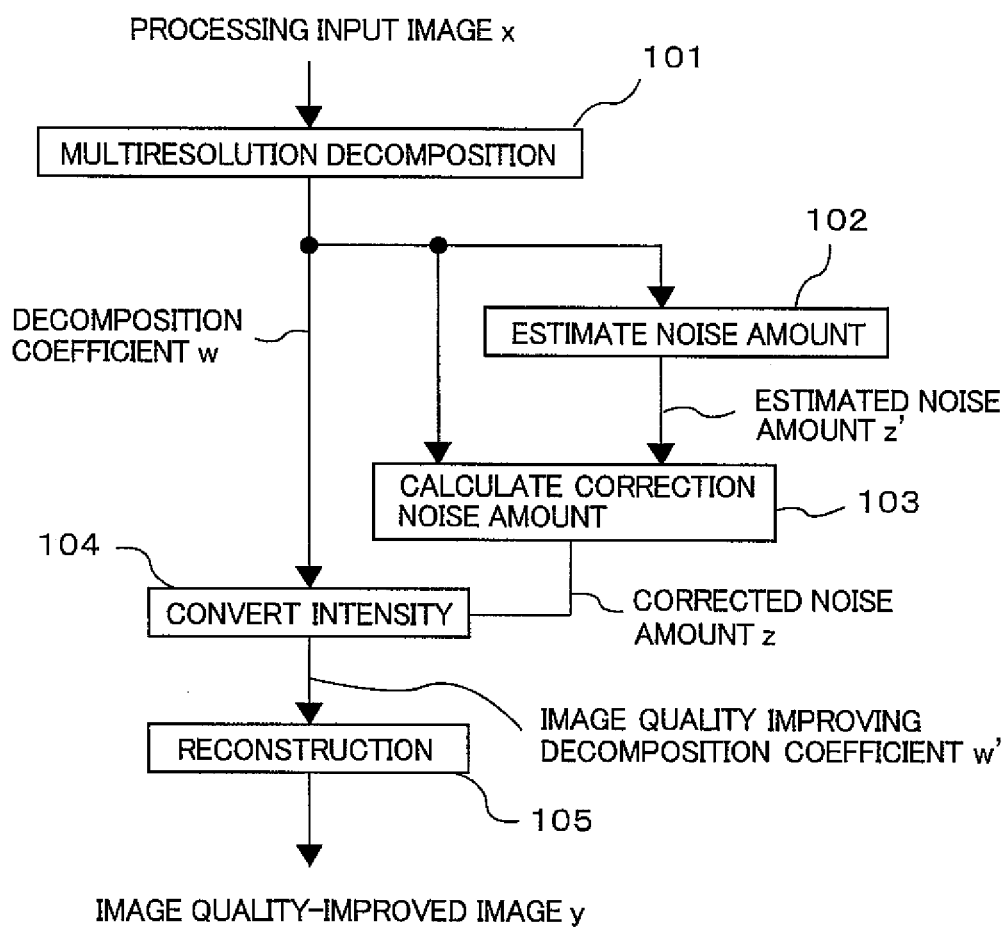
FIG. 1 is a chart tracing the flow of image quality improvement in an exemplary embodiment of the invention.

FIG. 1 shows the flow of image quality improvement in one exemplary embodiment of the invention. First, a resolution coefficient w is figured out by subjecting an input image to be processed x to multi-level resolution by multi-level resolution processing 101. The input image to be processed x is a vector having a scalar value x [m, n] for each position (m, n). The resolution coefficient w is a vector having a scalar value $w_{j,o}$ [m, n] for each position (m, n), each resolution level j and each edge direction o.

The resolution coefficient w generally has a value of a real number or a complex number for each resolution level, edge direction or position. Next, a corrected noise amount z is calculated by figuring out an estimated noise amount z' by noise amount estimation 102 and correcting the estimated noise amount by corrected noise amount calculation 103. If the estimated noise amount z' need not be corrected, the same value as the estimated noise amount z' may as well be outputted at the corrected noise amount calculation 103 as the corrected noise amount z. After that, the resolution coefficient w is subjected to intensity conversion as intensity conversion 104 on the basis of the corrected noise amount z. The resolution coefficient after the intensity conversion will be referred to as the image quality improving resolution coefficient w'. Finally, an image having gone through image quality improvement (hereinafter referred as the quality-improved image) y is obtained by reconstruction 105. The quality-improved image y, like the input image to be processed x, is a vector having a scalar value y [m, n] for each position (m, n). Also, the estimated noise amount z', the corrected noise amount z and the image quality improving resolution coefficient w', like the resolution coefficient w, is a vector having scalar values $z'_{j,o}[m, n]$, $z_{j,o}[m, n]$ and $w'_{j,o}[m, n]$ for each position (m, n), each resolution level j and each edge direction o.

Figure 2A:
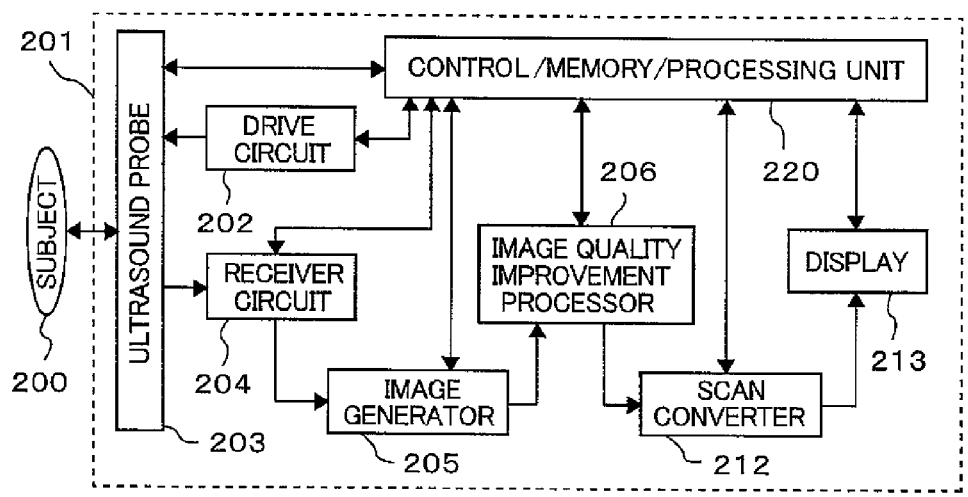
FIGS. 2(a)-2(d) are block diagrams illustrating the configuration an ultrasonographic device pertaining to the block diagrams illustrating the configuration of the exemplary embodiment of the invention.

Next, the configuration of an ultrasonographic device according to the invention will be described with reference to FIG. 2. FIG. 2(a) shows an exemplary embodiment of the configuration of an ultrasonographic device 201. The ultrasonographic device 201 is provided with an ultrasound probe 203 that transmits and receives ultrasound signals, a drive circuit 202 that generates drive signals to be inputted to the ultrasound probe 203, a receiver circuit 204 that carries out amplification and A/D conversion of received signals, an image generator 205 that generates an image in which sequences of ultrasound scanning line signals are arrayed two-dimensionally, an image quality improvement processor 206 that processes image quality improvement of signals, a scan converter 212 that processes coordinate conversion and interpolation of images expressed in scanning line signal sequences, a display 213 that displays the image generated by the scan converter, and a controller/memory/processing unit 220 that controls all these steps as well as stores and processes data.

The ultrasound probe 203 transmits to a subject 200 ultrasound signals based on the drive signals, receives reflected waves from the subject 200 that are obtained at the time of transmission and converts them into electrical received signals. The ultrasound probe 203 is available in such types as linear, convex, sector and radial types. Where the ultrasound probe 203 is of the convex type, the scan converter 212 converts a rectangular image into a sectorial image.

The image generator may so correct the position as to make the image obtained by performing transmission and reception in consecutive time frames identical as the displayed position of the tissue.

The image quality improvement processor 206, as shown in FIG. 2 (d), is provided with a multi-level resolving unit 207, a noise amount estimator 208, a noise amount corrector 209, an intensity converter 210 and a reconstructing unit 211, which perform in the respective blocks the multi-level resolution processing 101, the noise amount estimation 102, the corrected noise amount calculation 103, the intensity conversion 104 and the reconstruction 105 shown in FIG. 1.

Figure 2B:
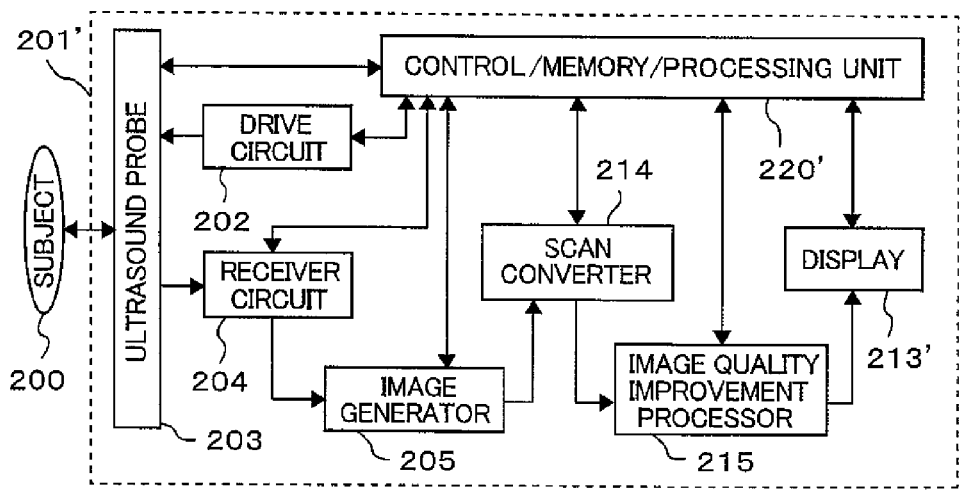
Figure 2C:
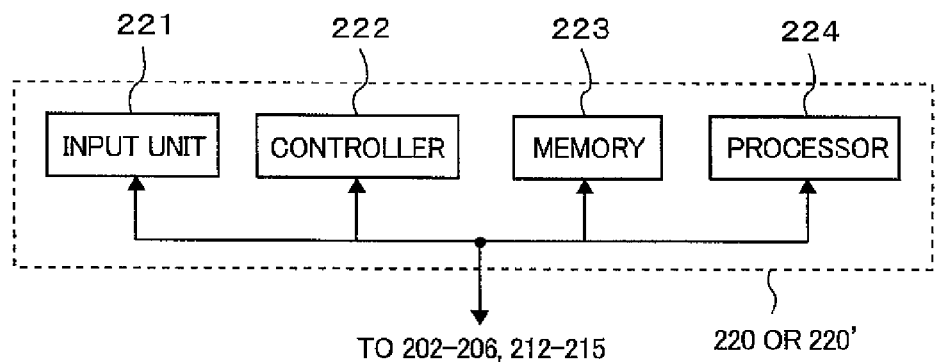
Figure 2D:
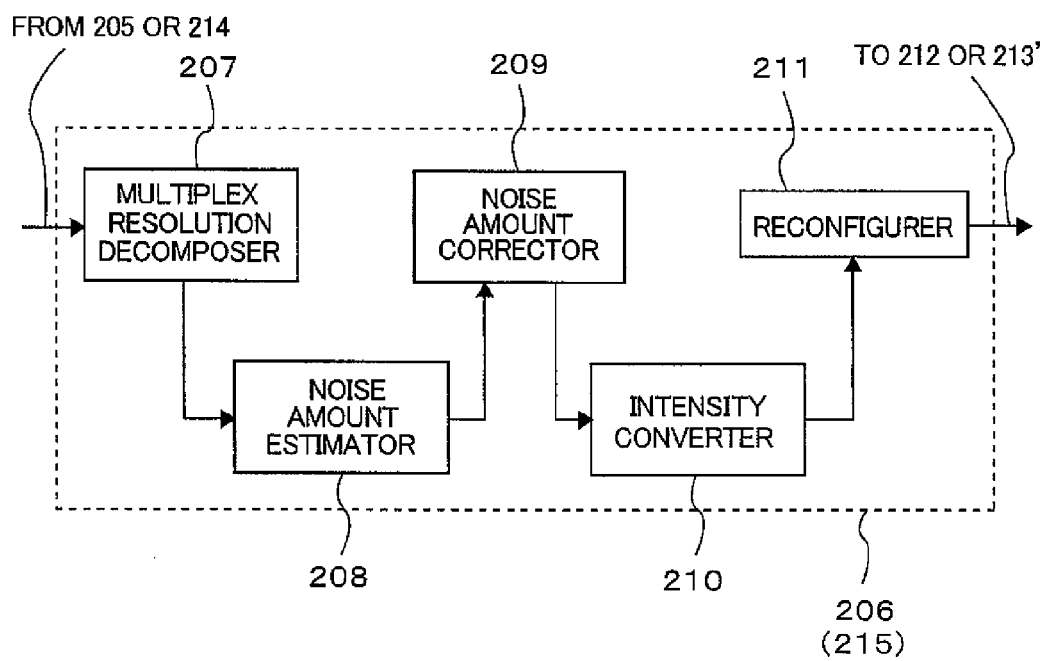

Further, the controller/memory/processing unit 220, as shown in FIG. 2(c), provided with an input unit 221, a controller 222, memory 223 and a processor 224, and parameters regarding the timing of image generation starting and the generation of an image among others are inputted from the input unit 221. The controller 222 controls the operations of the drive circuit 202, the ultrasound probe 203, the receiver circuit 204, the image quality improvement processor 206 and so forth. The memory 223 stores received signals, images generated by the image generator 205, resolution coefficients calculated by the image quality improvement processor 206, images having gone through image quality improvement, displayed images, which are the outputs of the scan converter 212 and the like. Tasks processed by the processor 224 include shaping of electrical signals for inputting to the ultrasound probe 203 and the adjustment of brightness and contrast at the time of displaying an image.

In the configuration described above, the ultrasound probe 203 transmits to the subject 200 ultrasound signals based on drive signals controlled by the controller 222 of the controller/memory/processing unit 220, receives reflected signals from the subject 200 which are obtained by this transmission, and converts them into electrical received signals.

Next, after the received signals converted into electrical signals are amplified by the receiver circuit 204 and undergo A/D conversion, these A/D-converted signals are processed by the image generator 205 to generate an image, which is inputted to the image quality improvement processor 206. In the image quality improvement processor 206, the inputted image undergoes as stated above the multi-level resolution processing 101, the noise amount estimation 102, the corrected noise amount calculation 103, the intensity conversion 104 and the reconstruction 105 to be processed for high-precision image quality improvement to provide a quality-improved image. Furthermore, by generating an image resulting from coordinate conversion and interpolation processing of this quality-improved image by the scan converter 212, a clearer ultrasound image reduced in noise components can be displayed on the screen of the display 213.

FIG. 2(b) shows another exemplary embodiment of the configuration of the ultrasonographic device according to the invention. In the configuration of the ultrasonographic device 201 shown in FIG. 2(b), the arrangement of a scan converter 214 and an image quality improvement processor 215 differs from that in the configuration of the ultrasonographic device 201 shown in FIG. 2(a). Meanwhile, the same elements in the configuration shown in FIG. 2 (b) as their counterparts in the configuration shown in FIG. 2(a) are assigned respectively the same reference numerals.

This ultrasonographic device 201' shown in FIG. 2(b) is provided with the ultrasound probe 203 that transmits and receives ultrasound signals, the drive circuit 202 that generates drive signals to be inputted to the ultrasound probe 203, the receiver circuit 204 that carries out amplification and A/D conversion of received signals, the image generator 205 that generates an image in which sequences of ultrasound scanning line signals are arrayed two-dimensionally, the scan converter 214 that processes coordinate conversion and interpolation of images generated by this image generator 205, an image quality improvement processor 215 that processes image quality improvement of images generated by the scan converter 214, the display 213' that displays the image having gone through picture improvement, and a controller/memory/processing unit 220' that controls all these steps as well as stores and processes data.

In the configuration shown in FIG. 2(a), the output image from the image generator 205 is an image having sequences of ultrasound scanning line signals expressed in parallel. For this reason, by subjecting the image generated by the image generator 205 to image quality improvement, any deterioration in image quality dependent on the scanning direction can be reduced. In the configuration shown in FIG. 2(b) on the other hand, the output image from the scan converter 214 takes on the same form as the image outputted to the display 213. For this reason, by subjecting the image generated by the scan converter 214 to image quality improvement, any deterioration in image quality that may arise in connection with coordinate conversion and interpolation processed by the scan converter 214 or any other fault can be kept to the minimum.

Next, multi-level resolution processed by the multi-level resolving unit 207 of the image quality improvement processor 206 or 215 will be described with reference to FIG. 3 and FIG. 4.

Figure 3A:
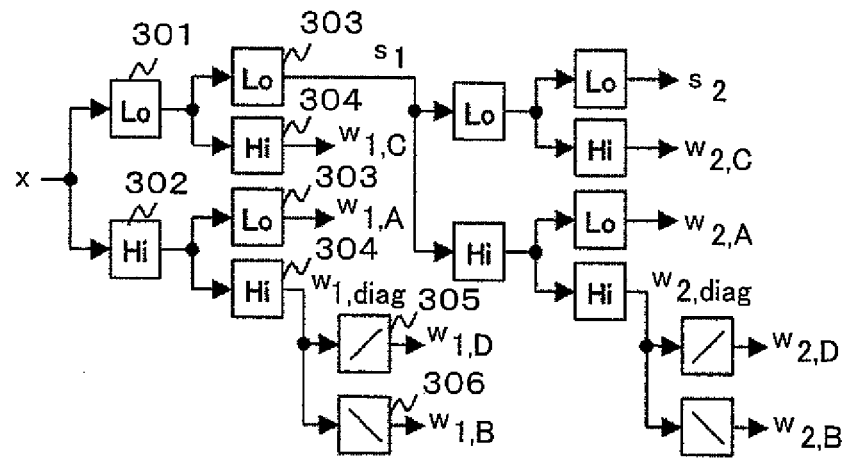
FIGS. 3(a)-3(c) are block diagrams illustrating the method of multi-level resolution.
Figure 3B:
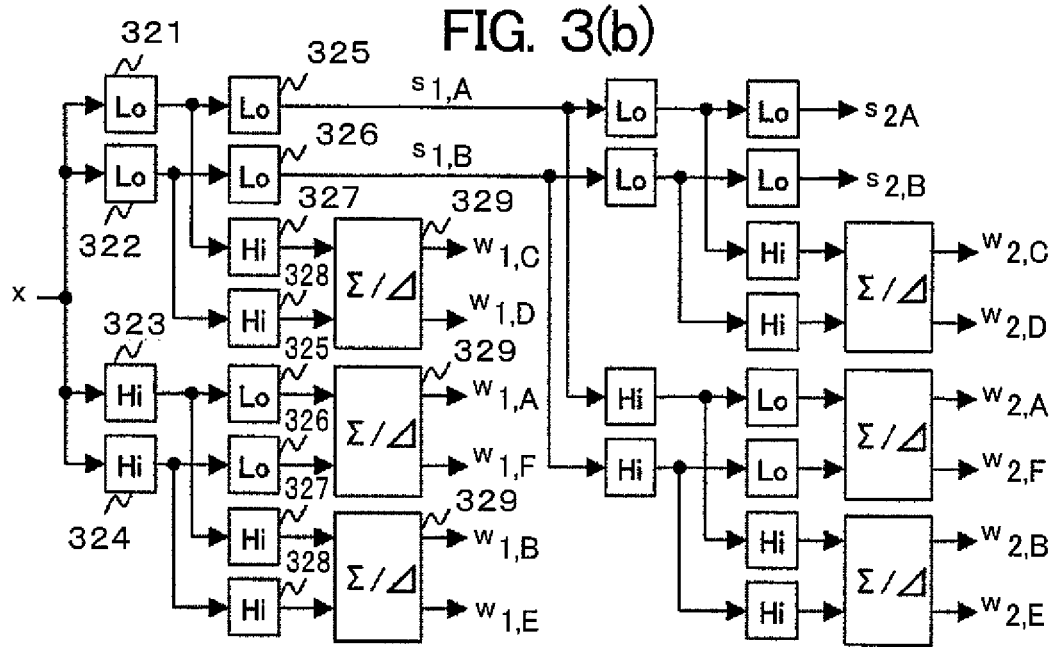
Figure 3C:
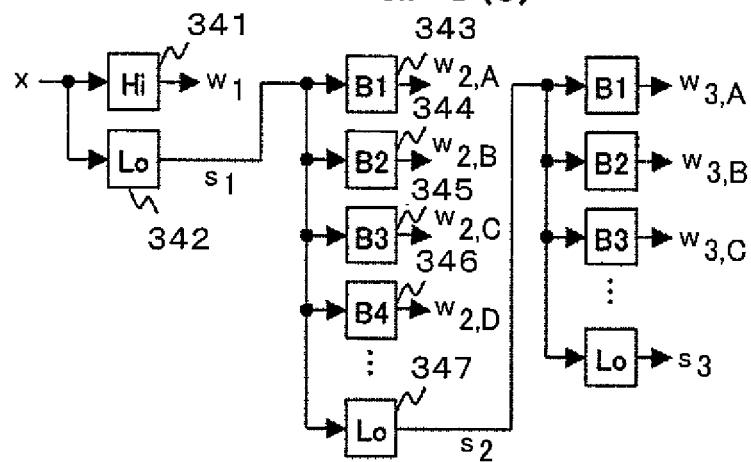

As stated above, known multi-level resolving systems include Wavelet transform, complex Wavelet transform, Curvelet transform, Contourlet transform and steerable pyramid transform systems. Exemplary embodiments of the invention, representing processing flows of multi-level resolution, are shown in FIG. 3. FIGS. 3(a), 3(b) and 3(c) show embodiments of processing flows of multi-level resolving systems respectively based on Wavelet transform, complex Wavelet transform and steerable pyramid transform having the edge direction divided into four or more.

To being with, the processing flow of the multi-level resolving system by Wavelet transform having the edge direction divided into four or more, which is an exemplary embodiment of the invention, shown in FIG. 3(a) will be described. First, after a horizontal (in the m direction) one-dimensional low-pass filter 301 and a horizontal one-dimensional high-pass filter 302 are applied to the input image to be processed x [m, n], a one-dimensional low-pass filter 303 and a high-pass filter 304 in a direction vertical (in the n direction) to the output signals of the foregoing filters are applied. The coefficients of these filters are real numbers. The sequence of applying the horizontal filters 301, 302 and the vertical filters 303, 304 may as well be reverse. Processing to withdraw every other pixel (hereinafter referred to as decimation) may be applied immediately after these steps of filtering. This results in resolution of the input image to be processed x into four different resolution coefficients $s_1$, $w_{1,C}$, $w_{1,A}$ and $w_{1,diag}$ of resolution level 1.

The resolution coefficient $s_1$ represents a component which is low in frequency both in the horizontal and in the vertical directions; $s_1$ is referred to as the low frequency resolution coefficient of resolution level 1. The resolution coefficient $w_{1,C}$ represents a component whose frequency is low in the horizontal direction and high in the vertical direction; the resolution coefficient $w_{1,A}$, a component whose frequency is high in the horizontal direction and low in the vertical direction, and the resolution coefficient $w_{1,diag}$, a component which is high in frequency both in the horizontal and in the vertical directions. The resolution coefficient $w_{1,C}$ strongly reacts to a high frequency edge in the horizontal edge while the resolution coefficient $w_{1,A}$ strongly reacts to a high frequency edge in the vertical direction. Further, whereas the resolution coefficient $w_{1,diag}$ strongly reacts to a high frequency edge, edges in a 45° oblique direction include two different edges, one parallel to a straight line m=n and the other parallel to a straight line m=−n.

Figure 4A:
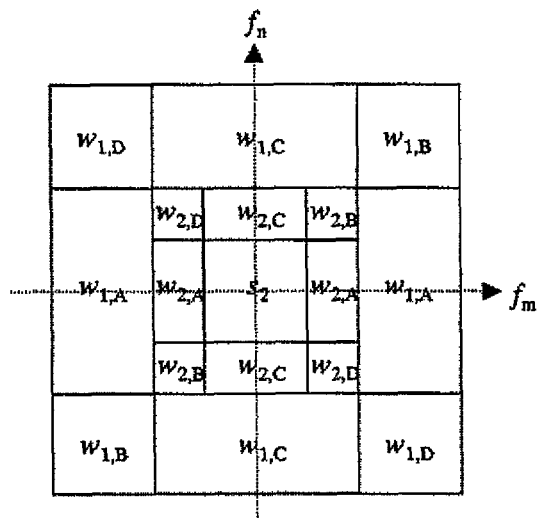
FIGS. 4(a)-4(c) illustrate the method of frequency division in multi-level resolution.

Then, by further applying a filter 305 that passes the edge parallel to the straight line m=n and cuts off the edge parallel to the straight line m=−n and a filter 306 that, conversely, cuts off the edge parallel to the straight line m=n and passes the edge parallel to the straight line m=−n, resolution coefficients $w_{1,D}$ and $w_{1,B}$ of resolution level 1 are calculated. The resolution coefficients $w_{1,A}$, $w_{1,B}$, $w_{1,C}$, and $w_{1,D}$ will be referred to as high frequency resolution coefficients of resolution level 1. FIG. 4(a) shows dominant frequency components in each resolution coefficient in a multi-level resolving system by Wavelet transform having the edge direction divided into four or more. The frequencies $f_m$ and $f_n$ respectively are horizontal and vertical frequencies. For instance, $w_{1,A}$ contains a greater proportion of components of which the horizontal frequency $f_m$ is high and the vertical frequency $f_n$ is low.

Then, by filtering the resolution coefficient $s_1$ in the same way as in the processing of the input image to be processed x, resolution coefficients $s_2$, $w_{2,A}$, $w_{2,B}$, $w_{2,C}$, and $w_{2,D}$ of resolution level 2 are calculated. Although FIG. 3(a) shows resolution coefficients of only up to resolution level 2, resolution coefficients of successively higher resolution levels are calculated by recurrently repeating the same processing. As shown in FIG. 4(a), the higher the resolution level of a resolution coefficient, the higher the proportion of its low frequency contents and the lower the frequency of those contents.

When the high frequency resolution coefficient of the highest resolution level calculated by multi-level resolution is $w_{J-1}$, J is referred to as the highest resolution level (J=3 in the example of (FIG. 3(a)). The low frequency resolution coefficient $s_{J-1}$ is represented by $w_{J-A}$, while the low frequency resolution coefficient $s_{J-1}=w_{J-A}$ is referred to as the resolution coefficient of resolution level J and the high resolution coefficient of resolution level j (j=1, . . . , J-1), as the resolution coefficient of that resolution level j. The resolution coefficient $w_{j,o}$ of resolution level j and edge direction o is a vector having scalar values $w_o[m, n]$ in each position (m, n). Further, the resolution coefficient at every resolution level is represented by w. Although the edge direction at resolution levels 1 and 2 is divided into four in FIG. 3(a), the edge direction need not be always divided into four, but there may be a resolution level at which the edge direction is divided into some other number than four. The same can be said of the cases in FIGS. 3(b) and 3(c) which will be described below.

Next, the processing flow of the multi-level resolving system by complex Wavelet transform, which is an exemplary embodiment of the invention, shown in FIG. 3(b) will be described. First, after horizontal (in the m direction) one-dimensional low-pass filters 321, 322 and horizontal one-dimensional high-pass filters 323, 324 to the input image to be processed x [m, n] area applied, one-dimensional low-pass filters 325, 326 and high-pass filters 327, 328 in a direction vertical (in the n direction) to the output signals of the foregoing filters are applied. Although filters of two different types each are used for each round of filter processing in this illustration of the exemplary embodiment, this is not the only applicable combination. The coefficients of these filters are usually complex numbers.

Figure 4B:
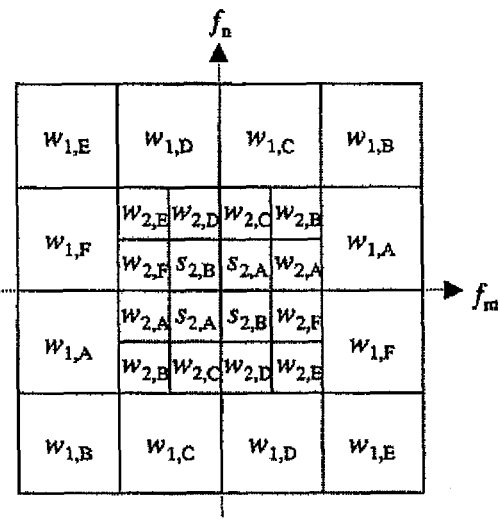

As in the case shown in FIG. 3(a), the sequence of applying the horizontal filters and the vertical filters may as well be reverse, and decimation may be applied immediately after these steps of filtering. The resolution coefficients $s_{1,A}$ and $s_{1,B}$ obtained by applying the horizontal one-dimensional low-pass, filter and the vertical one-dimensional low-pass filter will be referred to as low frequency resolution coefficients of resolution level 1. Next, processing to calculate the difference between the sum and balance between the two signals by a ΣΔ block 329 to other resolution coefficients than the calculated low frequency resolution coefficient, and frequency resolution coefficients $w_{1,A}$, $w_{1,B}$, $w_{1,C}$, $w_{1,D}$, $w_{1,E}$ and $w_{1,F}$ of high resolution level 1 are thereby calculated. Then, by filtering the low resolution coefficients $s_{1,A}$ and $s_{1,B}$ of resolution level 1 in the same way as in the processing of the input image to be processed x, resolution coefficients $s_{2,A}$, $s_{2,B}$, $w_{2,A}$, $w_{2,B}$, $w_{2,C}$, $w_{2,D}$, $w_{2,E}$ and $w_{2,F}$ of resolution level 2 are calculated. By applying recurrent processing hereafter, resolution coefficients of successively higher resolution levels are calculated. FIG. 4(b) shows dominant frequency components in each resolution coefficient in a multi-level resolving system by complex Wavelet transform. Six different high frequency resolution coefficients at each resolution level strongly react to six different edge directions.

Next, the processing flow of the multi-level resolving system by steerable pyramid transform, which is an exemplary embodiment of the invention, shown in FIG. 3(c) will be described. First, by applying two-dimensional high-pass filter 341 which cuts off only those components whose frequencies are low in both vertical and horizontal directions to the input image to be processed x [m, n], a high frequency resolution coefficient $w_1$ of resolution level 1 is calculated. Further, by applying a two-dimensional low-pass filter 342 which passes only those components whose frequencies are low in both vertical and horizontal directions to the input image to be processed x, a low frequency resolution coefficient $s_1$ of resolution level 1 is calculated. Decimation may be processed immediately after the two-dimensional low-pass filtering.

Next, by applying filters 343, 344, 345, 346, . . . which pass only those components of which the frequency is high and has a specific edge direction in either the vertical or horizontal direction to the resolution coefficient $s_1$, high frequency resolution coefficients $w_{2,A}$, $w_{2,B}$, $w_{2,C}$, $w_{2,D}$, . . . of resolution level 2 are calculated. Further, by applying a two-dimensional low-pass filter 347 to the resolution coefficient $s_1$, a low frequency resolution coefficient $s_2$ of resolution level 2 is calculated. Then, by filtering the resolution coefficients $s_2$ in the same way as in the processing of the resolution coefficient $s_1$, resolution coefficients $w_{3,A}$, $w_{3,B}$, $w_{3,C}$, . . . of resolution level 3 are calculated, followed by recurrent processing.

Figure 4C:
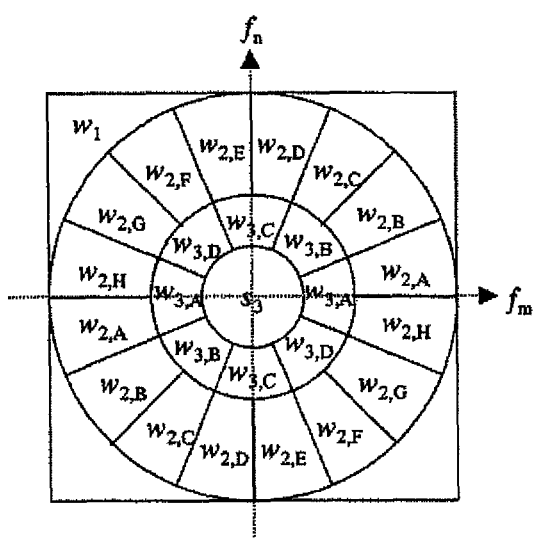

FIG. 4(c) shows dominant frequency components in each resolution coefficient in a multi-level resolving system by steerable pyramid transform. It has to be noted that, in the case shown in FIG. 4(c), the edge direction at resolution levels 2 and 3 is divided into eight and four, respectively. The processing parameters in the exemplary embodiment shown in FIG. 3 include the highest resolution level, the number by which the edge direction at each resolution level is divided, the edge direction to be divided, and the presence or absence of decimation after filtering. These processing parameters can be varied with imaging conditions (including the type and magnification of the ultrasound probe, the frequency used, the presence or absence of compounding, and the scanning pitch), the type of the image and the imaging object (the imaging conditions, the type of the image and the imaging object will hereinafter be collectively referred to as imaging information).

Next, processing regarding the calculation of the noise amount by the noise amount estimator 208 of the image quality improvement processor 206 or 215 will be described with reference to FIG. 5 through FIG. 6.

Figure 5:
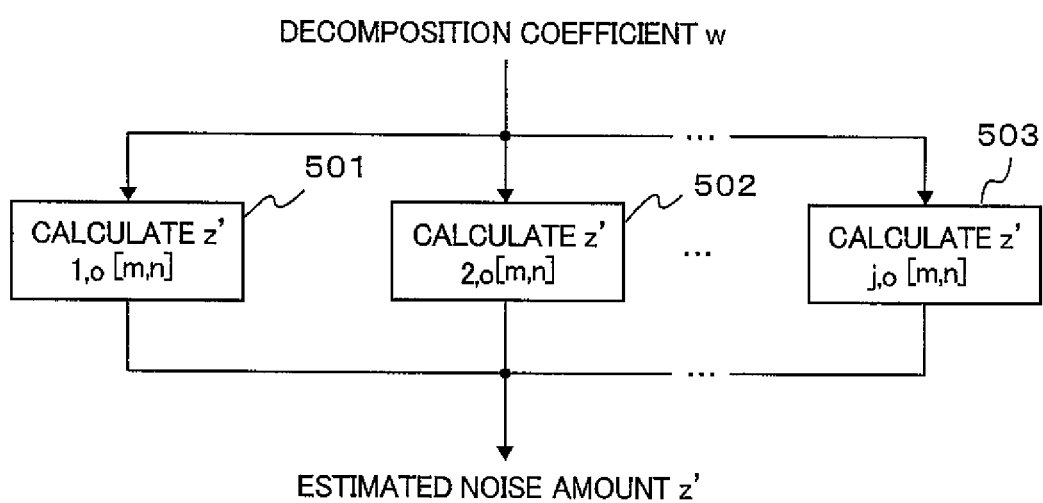
FIG. 5 is a flow chart showing the method of noise amount estimation.

FIG. 5 graphically describes the noise amount estimation 102 FIG. 1. Since the characteristics of noise contained in an ultrasound image usually vary with the position, resolution level and edge direction, it is effective to calculate the estimated noise amount for each position, resolution level and edge direction in order to process image quality improvement while appropriately suppressing noise. In the noise amount estimation shown in FIG. 5, the estimated noise amount z′ [m, n] at a resolution coefficient w [m, n] is calculated for each of multiple resolution levels j as represented by processing steps 501, 502 and 503. Herein, $w_{j,o}[m, n]$ and $z'_{j,o}[m, n]$ respectively represent the resolution coefficient and the estimated noise amount at or in the same resolution level j, edge direction o and position (m, n).

For instance, $z'_{j,o}[m, n]$ is calculated in the following manner as the standard deviation of the resolution coefficient in every edge direction and every position at the same resolution level j.

$$Z'_{j,o}[m, n] = Z'_j = \sum_{o',m',n'} |w_{j,o}[m, n]|^2 / N_j \quad \text{(Equation 1)}$$

Herein, $N_j$ is the number of resolution coefficients in every edge direction and every position at the resolution level j.

As another example, the following calculation is also by using the median of the absolute value of the resolution coefficient.

$$Z'_{j,o}[m, n] = Z'_j = \underset{o', m', n'}{\alpha \text{Median}} |W_{j,o'}[m', n']| \quad \text{(Equation 2)}$$

Herein, α is a constant. The estimated noise amount need not be calculated at every resolution level. In this case, a corrected noise amount is calculated by corrected noise amount calculation on the basis of estimated noise amounts at different resolution level.

Further, the estimated noise amount $z'_{j,o}$ need not be calculated for each of two or more edge directions or two or more positions (m, n) as in (Equation 1) or (Equation 2), and in this case z′ [m, n] is not dependent on the edge direction or the position (m, n). It is not always necessary to calculate estimated noise amounts for multiple resolution levels, and it is also permissible to calculate the estimated noise amount $z'_o$ [m, n] for each of multiple edge directions or of multiple positions. The processing parameters for use in noise amount estimation include parameters for determining the resolution level, edge direction and position for which the noise amount is to be estimated and a parameter for specifying the method of noise amount calculation, and these processing parameters can be varied according to imaging information.

Figure 6A:
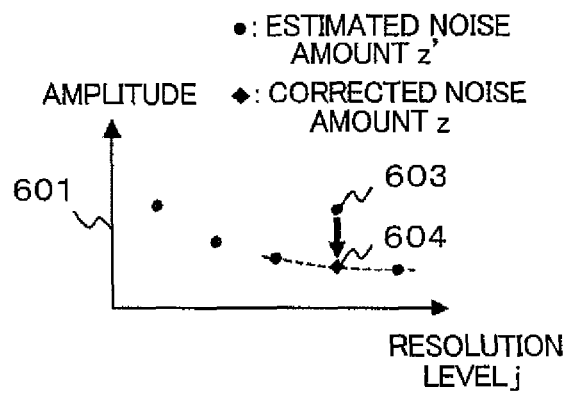
FIGS. 6(a)-6(c) illustrate the processing to calculate the corrected noise amount.
Figure 6A:
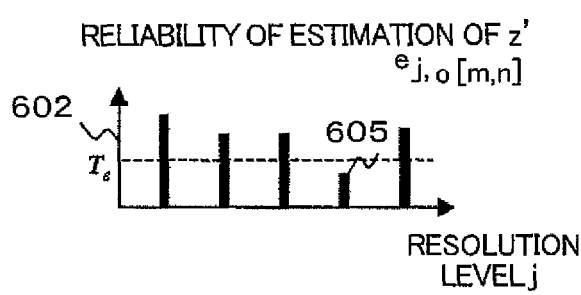

Next, the method of corrected noise amount calculation by the noise amount corrector 209 of the image quality improvement processor 206 or 215 will be described with reference to FIG. 6. Graph 601 in FIG. 6(a) shows the estimated noise amount $z'_{j,o}$ [m, n] and the corrected noise amount $z_{j,o}$ [m, n] at each resolution level in a specific edge direction o and position (m, n) in an exemplary embodiment of the corrected noise amount calculating method. Graph 602 shows the reliability of noise amount estimation (hereinafter referred as the reliability of estimation) $e_{j,o}$ [m, n] in the resolution level j, edge direction o and position (m, n) corresponding to the estimated noise amount $z'_{j,o}$ [m, n]. The reliability of estimation $e_{j,o}$ e. [m, n] can be calculated, for instance, from one or more estimated noise amounts, from the distance or the like between estimated noise amounts calculated by multiple methods such as (Equation 1) and (Equation 2), or on the basis of resolution coefficients in different frames of images, or a predetermined reliability value can be used. When a predetermined value is to be used, a table of such values may be prepared in advance so that an appropriate value can be used according to imaging information.

The corrected noise amount is calculated on the basis of the estimated noise amount and reliability. In the manner shown in FIG. 6(a) a threshold T is set with respect to reliability levels of estimation, and only an estimated noise amount 603 matching a reliability level of estimation 605, which is smaller than the threshold T, and a corrected noise amount 604 is calculated on that basis. Correction is accomplished by interpolation with respected to the pertinent estimated noise amount by using the numbers of neighboring positions and neighboring frequencies and the values of other estimated noise amounts in neighboring edge directions.

Figure 6B:
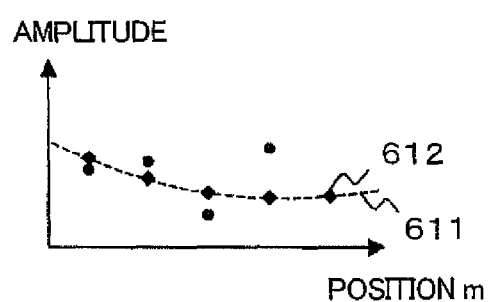
Figure 6B:
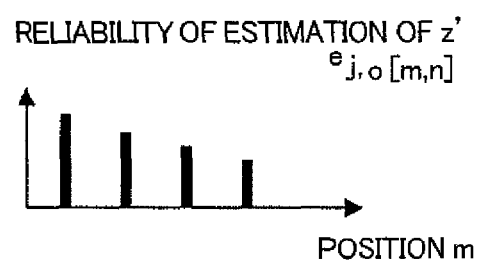

In the case graphed in FIG. 6(b), the estimated noise amount $z_{j,o}[m, n]$ and the corrected noise amount $z'_{j,o}[m, n]$ in each of the positions (m, n) (where n is fixed) in a specific edge direction o and at a resolution level j are shown. An approximate curve 611 is figured out for the estimated noise amount $z'_{j,o}$ [m, n], and a point on the figured-out approximate curve is supposed to represent the corrected noise amount. The approximate curve 611 is calculated on the basis of the reliability of estimation.

For instance, a curve that would minimize $E_z$ given by the following equation as the weighted least square approximation is selected.

$$E_z = \sum_{j',o',m',n'} e_{j',o'}[m', n'] \left( \frac{Z'_{j',o'}[m', n'] - }{Z'_{j',o'}[m', n']} \right)^2 \quad \text{(Equation 3)}$$

$Z'_{j',o}[m, n]$ here is a function representing the approximate curve 611, a function that can be represented by one or more parameters, a resolution level j′, an edge direction o′ and a position m′, n′.

The approximate curve 611 can be figured out by calculating the one or more parameters that would minimize the value of (Equation 3). The sum on the right side of (Equation 3) represents calculation of the sum with respect to the pertinent estimated noise amount in the neighboring positions m′, n′, the number of neighboring frequencies (resolution levels) j′ and neighboring edge directions o′. Further, as in the case of a corrected noise amount 612, a corrected noise amount can be calculated by interpolation or approximation even for a position where no estimated noise amount was calculated in the noise amount estimation with reference to FIG. 5.

Figure 6C:
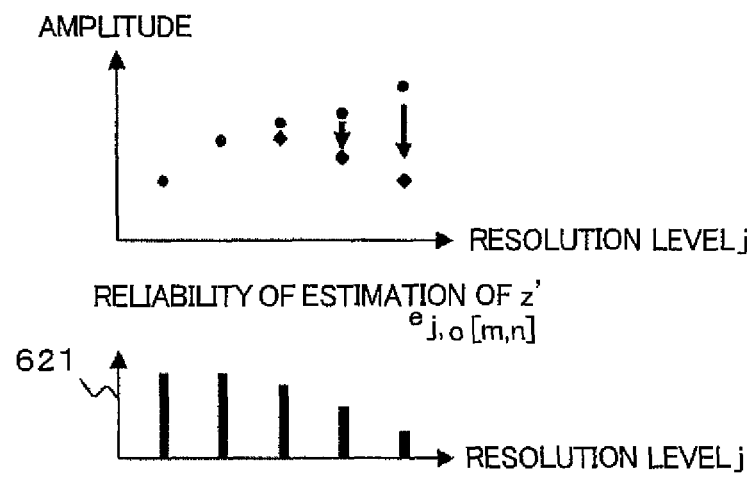

In the case shown in FIG. 6(c), the corrected noise amount $z_{j,o}[m, n]$ is figured out by using the product of a reliability of estimation $e_{j,o}[m, n]$ and the estimated noise amount $z'_{j,o}[m, n]$.

$$z_{j,o}[m,n] = e_{j,o}[m,n] z'_{j,o}[m,n] \quad \text{(Equation 4)}$$

This method is effective where the estimated noise amount becomes greater than the true noise amount with a decrease in the reliability of estimation. When noise amount estimation is processed by using (Equation 1) and (Equation 2), the calculation is affected by some signal components in the resolution coefficient, sometimes resulting in a greater estimated noise amount than its real noise amount.

Processing parameters for use in corrected noise amount calculation include parameters for identifying the reliability of estimation and parameters for specifying a particular method of correction on the basis of the reliability of estimation, and these processing parameters can be varied according to imaging information.

Next, intensity conversion by the intensity converter 210 of the image quality improvement processor 206 or 215 will be described with reference FIG. 7 through FIG. 12.

Figure 7A:
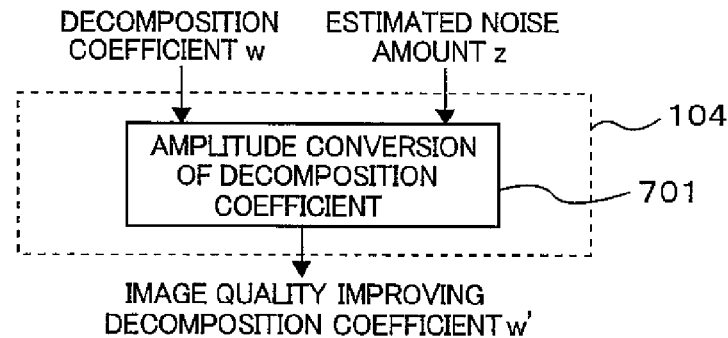
FIGS. 7(a)-7(c) are flow charts of intensity conversion.
Figure 7B:
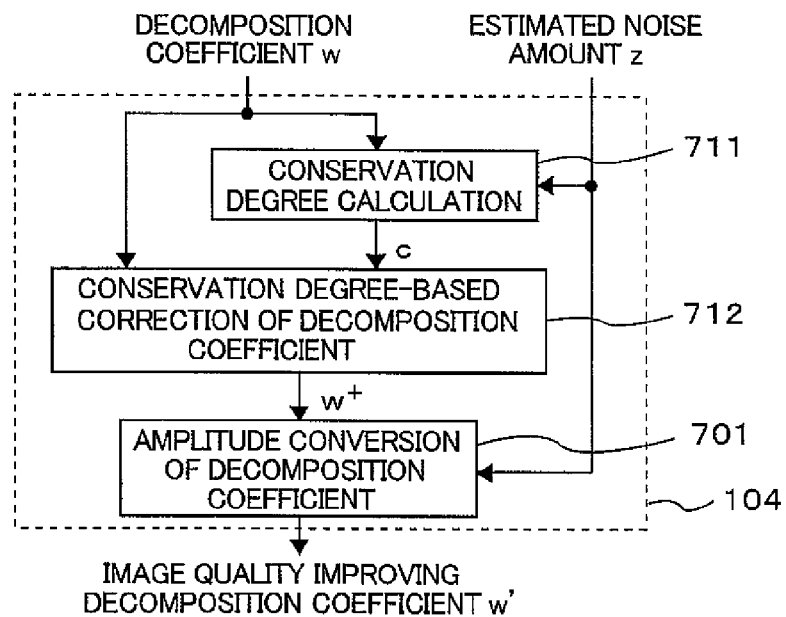
Figure 7C:
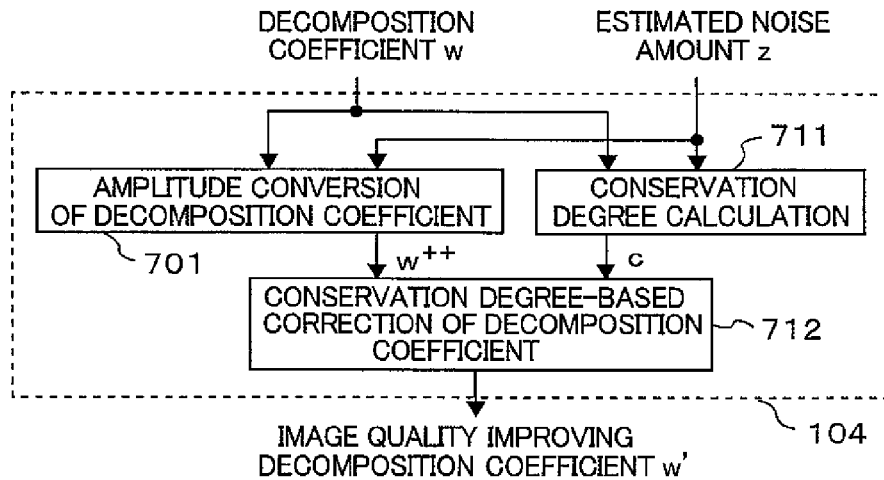

FIG. 7(*a*) shows a processing flow by the intensity conversion 104, which is one exemplary embodiment the invention. In this embodiment, an image quality improving resolution coefficient w' is generated by applying resolution coefficient amplitude conversion 701 to a resolution coefficient w. In the resolution coefficient amplitude conversion 701, the absolute value $|w'_{j,o}[m, n]|$ of the amplitude-converted resolution coefficient is calculated as expressed by the following equation as a function of the resolution coefficient $w_{j,o}[m, n]$ and the corrected noise amount $z_{j,o}[m, n]$ at or in the same resolution level j, edge direction o and position (m, n).

$$|w'_{j,o}[m,n]| = A(w_{j,o}[m,n]; z_{j,o}[m,n])$$ (Equation 5)

A(p;z) is an amplitude conversion function representing amplitude conversion. The amplitude conversion function A(p;z) is a function that monotonically increases with an input p.

FIGS. 8(*a*), 8(*b*) show examples of amplitude conversion function. A function 801 shown in FIG. 8(*a*) is an amplitude conversion function in the Soft Thresholding method, which is an extensively known amplitude conversion method.

$$A(p; z) = \begin{cases} |p| - T & \text{if } |p| \geq T \\ 0 & \text{if } |p| < T \end{cases}, T = kz$$ (Equation 6)

Herein, T is a multiple of the corrected noise amount z by a constant multiplier (e.g. T=3z, k=3).

A function 811 shown in FIG. 8(*b*) represents another example of amplitude conversion function. When the resolution coefficient amplitude conversion 701 gives $|w'_{j,o}[m, n]| > |w_{j,o}[m, n]|$, the signals are emphasized or, conversely, when it gives $|w'_{j,o}[m, n]| < |w_{j,o}[m,n]|$, the signals are restrained. Usually, when the resolution coefficient w[m, n] is a real number, the sign of the amplitude-converted resolution coefficient $w'_{j,o}[m, n]$ is made the same as that of the resolution coefficient $w_{j,o}[m, n]$, and when the resolution coefficient $w_{j,o}[m, n]$ is a complex number, the phase of $w'_{j,o}[m, n]$ is made the same as that of $w_{j,o}[m, n]$, but this is not always true.

Another embodiment of procession flow by the intensity conversion 104 is shown in FIG. 7(*b*). In this embodiment, conservation degree calculation 711 and resolution coefficient correction 712 based on the conservation degree is processed in addition to the resolution coefficient amplitude conversion 701. In the conservation degree calculation 711, a conservation degree C representing of the degree of conserving resolution coefficients is calculated on the basis of the estimated noise amount z and the values of multiple resolution coefficients, followed by correction, based on the conservation degree C, of each resolution coefficient w by the resolution coefficient correction 712 based on the conservation degree. The conservation degree C and the corrected resolution coefficients w' are vectors having scalar values $C_{j,o}[m, n]$ and $W^+_{j,o}[m, n]$ for each position (m, n), each resolution level j and each edge direction o. In the following description, a vector having a scalar value $a_{j,o}[m, n]$ for the position (m, n), resolution level j and edge direction o will be represented by simply a.

The corrected resolution coefficient $w^+_{j,o}[m, n]$ can be represented by the following equation as a function of the conservation degree $C_{j,o}[m, n]$ and the resolution coefficient $w_{j,o}[m, n]$ at the same resolution level j, edge direction 0, position (m, n).

$$w'_{j,o}[m,n] = F(C_{j,o}[m,n]w_{j,o}[m,n])$$ (Equation 7)

Herein, $F(C_{j,o}[m, n])$ is a monotonically increasing function. An example of $F(C_{j,o}[m, n])$ is shown in FIG. 9. If $F(C_{j,o}[m, n]) > 1$, the corrected resolution coefficient $w^+_{j,o}[m, n]$ will be greater than the uncorrected resolution coefficient $w_{j,o}[m, n]$.

In the resolution coefficient amplitude conversion 701, the amplitude-converted resolution coefficient $w'_{j,o}[m, n]$ is calculated by using the following (Equation 8) instead of (Equation 5).

$$w_{j,o}[m,n] = A(w'_{j,o}[m,n]; z_{j,o}[m,n])$$ (Equation 8)

Regarding this processing flow in the intensity conversion 104, another exemplary embodiment is shown in FIG. 7(*c*). In this embodiment, first the resolution coefficient amplitude conversion 701 and the conservation degree calculation 711 are processed. In the resolution coefficient amplitude conversion 701, an amplitude-converted resolution coefficient w" is calculated by using (Equation 9).

$$w''_{j,o}[m,n] = A(w_{j,o}[m,n]; z_{j,o}[m,n])$$ (Equation 9)

Further in the conservation degree calculation 711, the conservation degree C is calculated on the basis of the values of multiple resolution coefficients. Then, the resolution coefficient correction 712 is processed on the basis of the conservation degree C. By this processing, the corrected resolution coefficient $w'_{j,o}[m, n]$ is calculated as expressed in the following equation.

$$w'_{j,o}[m,n] = F(C_{j,o}[m,n])w''_{j,o}[m,n]$$ (Equation 10)

In the conservation degree-based resolution coefficient correction 712 charted in FIGS. 7(*b*) and 7(*c*), there is no need to correct all the resolution coefficients, no correction may be applied to, for instance, the resolution coefficient $w_j$ of a resolution level J, with $F(C_{j,o}[m, n])=1$ being supposed. Processing parameters in the intensity conversion in the exemplary embodiments charted in FIG. 7 include parameters for determining the choice of processing to be applied out of FIGS. 7(*a*), 7(*b*) and 7(*c*) for instance, and parameters for specifying the processing by each of the resolution coefficient amplitude conversion 701, the conservation degree calculation 711 and the conservation degree-based resolution coefficient correction 712, and these processing parameters can be varied according to imaging information.

Next, the conservation degree calculation 711 charted in FIG. 7 will be described with reference to FIG. 10 through FIG. 12.

First, a method of intensity conversion using multiple resolution coefficients will be described with reference to FIG. 10. FIG. 10(*a*) shows an example of relationship between the amplitude the position m of the high frequency resolution coefficient $w_{j,o}[m, n]$. In edge parts, the amplitude of the resolution coefficient in the corresponding edge direction o generally tends to be greater. A curve 1001 represents the amplitude of the resolution coefficient obtained when, supposing that signal components and noise components have been correctly separated from each other, only the signal components have been extracted on an edge 1004. The amplitude of the resolution coefficient $w_{j,o}[m, n]$ actually obtained from a picked-up image is affected by noise and therefore is off the curve 1001 usually. As a result, the value may prove smaller than that on the curve as is the case with a resolution coefficient 1002. On the other hand in a flat part 1005, the amplitude of the resolution coefficient is small because signal components contained in the resolution coefficient $w_{j,o}[m, n]$ are generally less. However, the amplitude may be irregularly increased by the impact of noise as is the case with a resolution coefficient 1003.

Figure 10A:
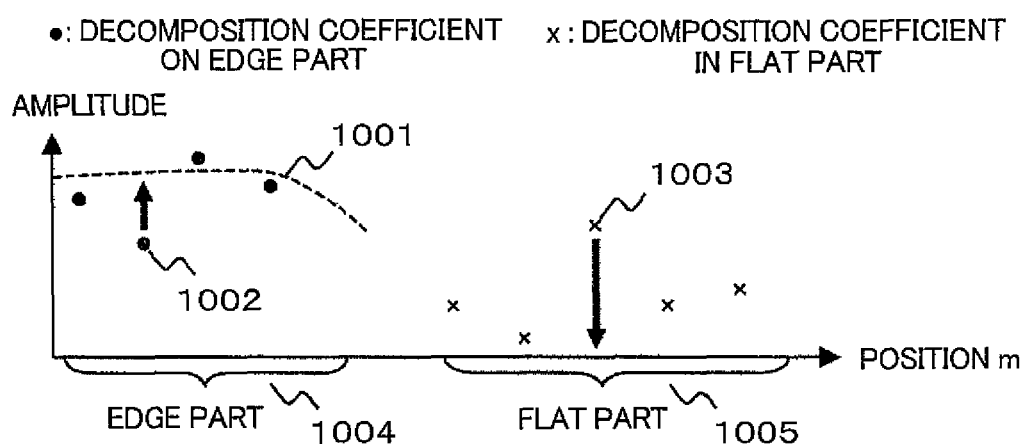
FIGS. 10(a)-10(c) illustrate coefficient intensity conversion of based on multiple resolution coefficients.
Figure 10B:
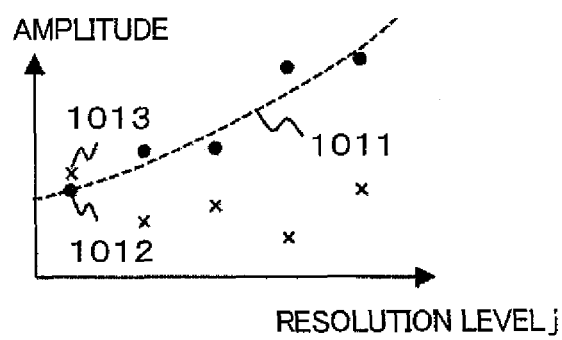
Figure 10C:
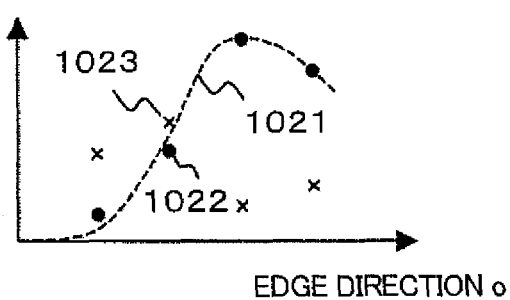

In the case shown in FIG. 10(*a*), in order to sufficiently improve image quality, it is effective to conserve the amplitude or increase the amplitude for the resolution coefficient 1002 which represents an edge part and, conversely, to decrease the amplitude for the resolution coefficient 1003 which represents a flat part. Therefore, note being taken of the generally greater presence of high amplitude resolution coefficients in positions near the resolution coefficient 1002 which represents an edge part and, conversely, the generally lower amplitude of resolution coefficients in positions near the resolution coefficient 1003 which represents a flat part, one exemplary embodiment of the invention is characterized by processing of intensity conversion utilizing the values of multiple resolution coefficients in nearby positions. Such processing cannot be realized by using only the amplitudes of individual resolution coefficients for intensity conversion, and this exemplary embodiment of the invention makes possible image quality improvement of higher precision than was previously achieved.

While a method of achieving satisfactory image quality improvement by utilizing the relevance of resolution coefficients in nearby positions was described with reference to FIG. 10(*a*), it is also effective to utilize the relevance of resolution coefficients at different resolution levels or in different edge directions. FIG. 10(*b*) shows an example of relationship between the amplitude and the resolution level of resolution coefficients. Points marked with o in the graph represent resolution coefficients in edge parts, while points marked with x represent resolution coefficients in flat parts. A curve 1011 represents, where it is supposed that signal components and noise components have been correctly separated from each other, the amplitude of the resolution coefficient obtained when only signal components are extracted in edge parts. Although the amplitude is generally greater in edge parts than in flat parts, sometimes the impact of noise makes the resolution coefficient in flat parts (e.g. a resolution coefficient 1013) greater than the resolution coefficient in edge parts (e.g. a resolution coefficient 1012). However, by using multiple resolution coefficients including resolution coefficients at different frequency levels, it is made possible to achieve image quality improvement of higher precision than was previously achieved.

Further, an example of relationship between the amplitude and the edge direction of resolution coefficients is shown in FIG. 10(*c*). Similarly, by utilizing the values of multiple resolution coefficients including resolution coefficients in nearby edge directions, processing to increase the amplitude of a resolution coefficient 1022, for instance, in edge parts and decrease that of a resolution coefficient 1023 in flat parts can be made possible. In this way, the exemplary embodiment of the invention makes possible enhanced performance image quality improvement by relevance among multiple resolution coefficients.

Next, conservation degree calculation referred to concerning FIGS. 7(*b*) and 7(*c*) will be described with reference to FIG. 11. The calculation of the conservation degree C uses the values of multiple resolution coefficients. FIG. 11(*a*) charts one exemplary embodiment of conservation degree calculation.

First in this embodiment, values $C^L$, $C^O$ and $C^S$ are figured out by blocks 1101, 1102 and 1103. The value $C^L$ here is calculated by the following equation as a function of resolution coefficients $w_{1,o}[m, n], \ldots, w_{J,o}[m, n]$ of different resolution levels in the same edge direction o and position (m, n).

$$C_{j,o}^L[m,n]=C^L(j;w_{1,o}[m,n],\ldots,w_{J,o}[m,n]) \qquad \text{(Equation 11)}$$

Herein, $C^L(\ldots)$ is a function, represented by $$C_{j,o}^L[m,n] = \begin{cases} \max\begin{pmatrix} w_{j,o}[m,n], \\ w_{j+L0}[m,n] \end{pmatrix} & \text{if } j < J \\ w_{j,o}[m,n] & \text{if } j = J \end{cases} \qquad \text{(Equation 12)}$$

for instance.

Since an input image to be processed x generally has more of signal components among lower frequency components, signals and noise can be distinguished from each other with high precision by using a resolution coefficient at a higher resolution level matching a lower frequency f than the pertinent resolution level j as in (Equation 12). Further, as in the calculation of $C^L$, the value $C^O$ is calculated as a function of resolution coefficients $w_{j,A}[m, n] \ldots, w_{j,K}[m, n]$ at or in the same resolution level j and position (m, n) in different edge directions.

$$C_{j,o}^O[m,n]=C^O(o;w_{j,A}[m,n],\ldots,w_{j,K}[m,n]) \qquad \text{(Equation 13)}$$

K is the number by which the edge direction is divided at the resolution level j. $C^L(\ldots)$ is a function, represented by $$C_{j,o}^O[m,n]=\max(w_{j,o1}[m,n],w_{j,o}[m,n],w_{j,o2}[m,n] \qquad \text{(Equation 14)}$$

for instance. Herein, $o_1$ and $o_2$ represent edge directions adjoining the edge direction o on two sides.

Further, the value $C^S$ is calculated by the following equation as a function of resolution coefficients $w_{1,o}[m^{(1)}, n^{(1)}], \ldots, w_{J,o}[m^{(5)}, n^{(5)}]$ at or in the same resolution level j and edge direction o and in different positions.

$$C_{j,o}^S[m,n]=C^S(m,n;w_{j,o}[m^{(1)},n^{(1)}],\ldots,\\ w_{j,o}[m^{(5)},n^{(5)}]) \qquad \text{(Equation 15)}$$

Herein, $w_{1,o}[m^{(1)}, n^{(1)}], \ldots, w_{J,o}[m^{(5)}, n^{(5)}]$ represent resolution coefficients in all the positions at the resolution level j and in the edge direction j. $C^S(\ldots)$ is a function, by which, a weighted average such as $$C_{j,o}^S[m, n] = \sum_{m'n'} a_{j,o}[m', n']w_{j,o}[m-m', n-n'] \qquad \text{(Equation 16)}$$

is calculated by using a specific weight $a_{j,o}[m', n']$.

FIG. 12 shows an exemplary embodiment representing the specific weight $a_{j,o}[m', n']$. By using $a_{j,o}[m', n']$ having a non-zero value in the edge direction, weight averaging is made possible along the edge direction. Since signal components, such as a tissue structure, contained in an image, generally have similar brightness values in the edge direction, the matching resolution coefficients also have substantially the same values in the edge direction. Therefore, by processing smoothing in the edge direction as shown in FIG. 12, noise components can be restrained without deteriorating signal components.

Incidentally, where decimation is to be processed after low-pass filtering or high-pass filtering as charted in FIG. 3, depending on the position (m, n), the values of some of the resolution coefficients $w_{1,o}[m, n], \ldots, w_{J,o}[m, n]$ at all the resolution levels in the position (m, n) may fail to be obtained. In such a case, conservation degree calculation is processed after figuring out the values of the required resolution coefficients by such processing as approximation with the resolution coefficient in the nearest position or processing interpolation with multiple resolution coefficients in nearby positions.

Further, where a multi-level resolving system differing with the resolution level in the number by which the edge direction is divided, depending on the edge direction o, the values of some of the resolution coefficients $w_{1,o}[m, n], \ldots, w_{J,o}[m, n]$ at all the frequency levels in the edge direction o may fail to be obtained. Similarly in such a case, conservation degree calculation is processed after figuring out the values of the required resolution coefficients by such processing as approximation with the resolution coefficient in the nearest edge direction or processing interpolation with multiple resolution coefficients in nearby edge direction. Also, each of $C^L$, $C^O$ and $C^S$ can be made a function always repeating a constant value or a function simply repeating $w_{j,o}[m, n]$.

Next, in a block 1104 of FIG. 11, the conservation degree C is calculated as represented by the following equation by using values $C^L_{j,o}[m, n]$, $C^O_{j,o}[m, n]$ and $C^S_{j,o}[m, n]$ at or in the same resolution level j, edge direction o and position (m, n).

$$C_{j,o}[m,n]=C(C^L_{j,o}[m,n],C^O_{j,o}[[m,n],C^S_{j,o}[m,n]]) \quad \text{(Equation 17)}$$

C( . . . ) is a function, represented by $$C(C^L_{j,o}[m,n],C^O_{j,o}[m,n],C^S_{j,o}[m,n])=(C^L_{j,o}[m,n]+C^O_{j,o}[m,n]+C^S_{j,o}[m,n])/3 \quad \text{(Equation 18)}$$

for instance.

Figure 11A:
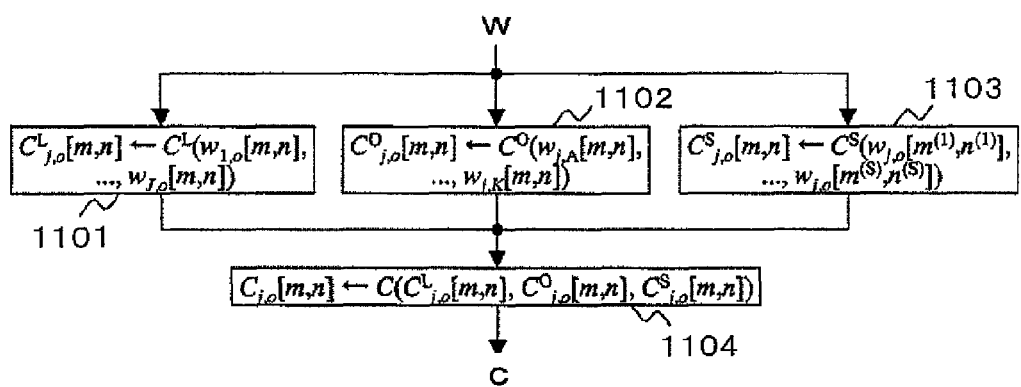
FIGS. 11(a)-11(c) are flow charts of conservation degree calculation.
Figure 11B:
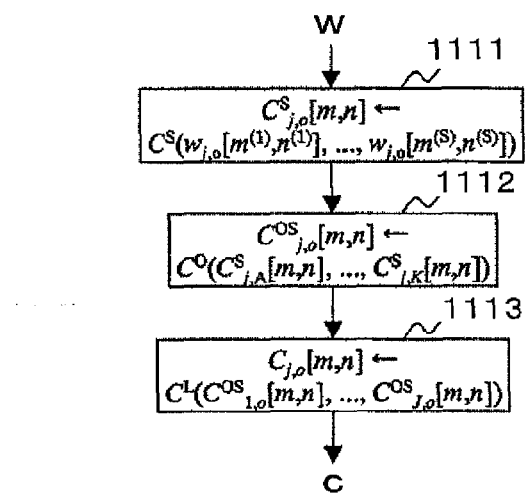

Although the functions $C^L(\ldots)$, $C^O(\ldots)$ and $C^S(\ldots)$ are used in parallel in the exemplary embodiment charted in FIG. 11(a), the functions $C^L(\ldots)$, $C^O(\ldots)$ and $C^S(\ldots)$ may as well be used in series as in another embodiment representing conservation degree calculation charted in FIG. 11(b). In the embodiment of FIG. 11(b), first in a block 1111, the value $C^S$ is calculated by the method represented by (Equation 15) as a function of resolution coefficients $w_{j,o}[m^{(1)}, n^{(1)}], \ldots, w_{j,o}[m^{(5)}]$ at or in the same resolution level j and edge direction o in different positions. Next in a block 1112, the following value $C^{OS}$ is calculated by using the function $C^O(\ldots)$ like the one used in (Equation 13) from values $C^S_{j,A}[m, n], \ldots, C^S_{j,K}[m,n]$ at or in the same resolution level j and position (m, n) in different edge directions.

$$C^{OS}_{j,o}[m,n]=C^O(o;C^S_{j,A}[m,n],\ldots,C^S_{j,K}[m,n]) \quad \text{(Equation 19)}$$

Then in a block 1113, the conservation degree C is calculated by using the function $C^L(\ldots)$ like the one used in (Equation 11) from values $C^{OS}_{1,o}[m, n], \ldots, C^{OS}_{J,o}[m, n]$ in the same edge direction and position (m, n) at different resolution levels.

$$C_{j,o}[m,n]=C^L(j;C^{OS}_{1,o}[m,n],\ldots,C^{OS}_{J,o}[m,n]) \quad \text{(Equation 20)}$$

Incidentally, the functions are brought to work on the resolution coefficients w in the sequence of $C^S(\ldots)$, $C^O(\ldots)$ and $C^L(\ldots)$ in the embodiment charted in FIG. 11(b), this sequence is not the only possible choice.

Figure 11C:
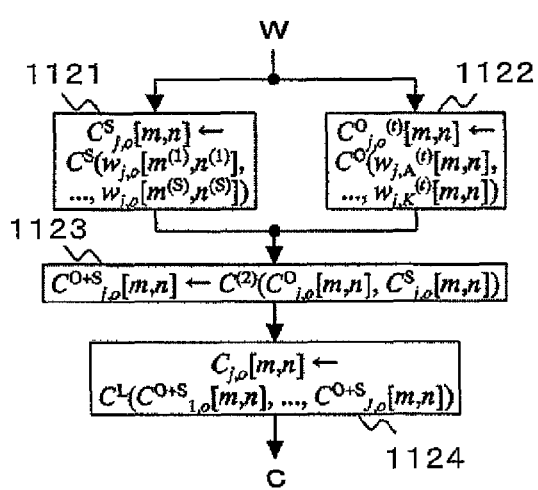

FIG. 11(c) charts another exemplary embodiment representing conservation degree calculation. Processing using the functions $C^L(\ldots)$, $C^O(\ldots)$ and $C^S(\ldots)$ in parallel and processing using the same in series are combined. First, after calculating the values $C^S$ and $C^O$ in blocks 1121 and 1122 by using (Equation 15) and (Equation 13), a value $C^{O+S}$ is calculated in a block 1123 as represented by the following equation by using values $C^O_{j,o}[m, n]$ and $C^S_{j,o}[m, n]$ at or in the same resolution level j, edge direction o and position (m, n).

$$C^{O+S}_{j,o}[m,n]=C^{O+S}(C^O_{j,o}[m,n],C^S_{j,o}[m,n]) \quad \text{(Equation 21)}$$

C( . . . ) is a function, represented by $$C^{O+S}(C^O_{j,o}[m,n],C^S_{j,o}[m,n])=(C^O_{j,o}[m,n]+C^S_{j,o}[m,n])/2 \quad \text{(Equation 22)}$$

for instance.

Then in a block 1124, the conservation degree C is calculated by using the function $C^L(\ldots)$ like the one used in (Equation 11) from values $C^{O+S}_{1,o}[m, n], \ldots, C^{O+S}_{J,o}[m, n]$ in the same edge direction and position (m, n) at different resolution levels.

$$C_{j,o}[m,n]=C^L(j;C^{O+S}_{1,o}[m,n],\ldots,C^{O+S}_{J,o}[m,n]) \quad \text{Equation 23}$$

Incidentally, in the embodiment charted in FIG. 11(c), though the function $C^L(\ldots)$ is used in series after the functions $C^S(\ldots)$ and $C^O(\ldots)$ are used in parallel, this is not the only possible combination.

Next, conservation degree calculation using resolution coefficients for images in different frames will be described with reference to FIG. 13 and FIG. 14.

FIG. 13 shows the relationship between the amplitude and the frame u of a high frequency resolution coefficient $w^{(u)}_{j,o}[m, n]$. The resolution coefficient obtained by subjecting multi-level resolution to an image shot in the frame u is referred to here as $w^{(u)}_{j,o}[m, n]$. Further, the frame to be subjected to image quality improvement is referred to as the frame t, and the resolution coefficient $w^{(u)}_{j,o}[m, n]$ is abbreviated to simply $w_{j,o}[m, n]$. In the following description, a vector having a scalar value $a^{(t)}_{j,o}[m, n]$ for the position (m, n), resolution level j, edge direction o and frame u will be represented by simply a.

Points marked with o in FIG. 13 represent resolution coefficients in edge parts, while points marked with x represent resolution coefficients in flat parts. A curve 1301 represents, where it is supposed that signal components and noise components have been correctly separated from each other, the amplitude of the resolution coefficient obtained when only signal components are extracted in edge parts. As the amplitude of the resolution coefficient $w^{(u)}_{j,o}[m, n]$ actually obtained from a picked-up image is affected by noise, it may become smaller than on the curve 1301 as is that of a resolution coefficient 1302. On the other hand, flat parts generally not containing much of signal components may sometimes be affected by noise, and the amplitude may increased as is that of a resolution coefficient 1303.

In order to improve image quality, it is necessary to conserve the amplitude or increase the amplitude for the resolution coefficient 1302 which represents an edge part and, conversely, to decrease the amplitude for the resolution coefficient 1303 which represents a flat part, but a method of intensity conversion using only the amplitudes of individual resolution coefficients cannot achieve the purpose. In contrast, in one exemplary embodiment of the invention, note is taken of the fact that in the expansion coefficient of nearby frames at or in the same resolution level, same edge direction and same position as the resolution coefficient 1302 representing an edge part the amplitude is generally higher while, conversely in the expansion coefficient of nearby frames at or in the same resolution level, same edge direction and same position as the resolution coefficient 1303 representing a flat part, the amplitude is generally lower, intensity conversion is processed by using the values of multiple resolution coefficients including resolution coefficients in nearby frames. This makes possible enhancement of the precision of distinguishing signal components and noise components from each other.

Figure 14A:
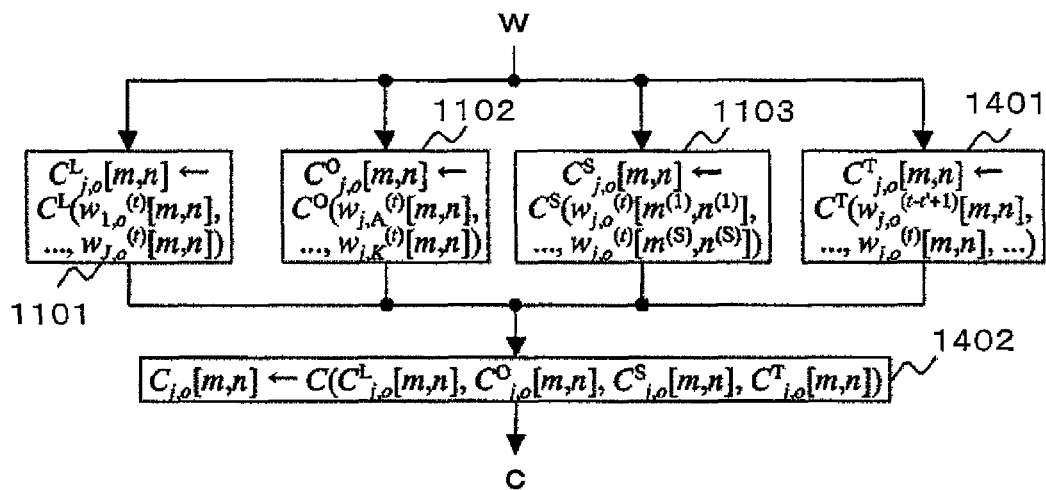
FIGS. 14(a), 14(b) are flow charts of conservation degree calculation using resolution coefficient in multiple nearby frames.

Next, conservation degree calculation in one exemplary embodiment of the invention will be described with reference to FIG. 14. In the embodiment charted in FIG. 14, similar processing to that of FIG. 11 is performed, but it is different from the embodiment of FIG. 11 in that the conservation degree is calculated by using the resolution coefficients of multiple frames. FIG. 14(a) charts an exemplary embodiment of conservation degree calculation. In this embodiment, values $C^T$, $C^L$, $C^O$ and $C^S$ are figured out in blocks 1101, 1102, 1103 and 1401. Herein, the value $C^T$ is calculated by the method represented by the following equation as a function of resolution coefficients $w_{j,o}^{(t-t'+1)}[m,n]$, $w_{j,o}^{(t-t'+2)}[m,n]$, ..., $w_{j,o}^{(t)}[m,n]$ of frames at or in the same resolution level j, edge direction o and positions (m, n).

$$C_{j,o}^T[m,n]=C^T(w_{j,o}^{(t-t'+1)}[m,n],w_{j,o}^{(t-t'+2)}[m,n],\ldots,w_{j,o}^{(t)}[m,n]) \quad \text{(Equation 24)}$$

Here, $C^T(\ldots)$ is a function, represented by $$C_{j,o}^T[m,n]=\text{Median}(w_{j,o}^{(t-t'+1)}[m,n],w_{j,o}^{(t-t'+2)}[m,n],\ldots,w_{j,o}^{(t)}[m,n]) \quad \text{(Equation 25)}$$

for instance. The value t' in (Equation 24) need not be a constant, but may as well be a variable.

Next in a block 1402, the conservation degree C is calculated by the following equation using the values $C^L$, $C^O$, $C^S$ and $C^T$.

$$C_{j,o}[m,n]=C^{(4)}(C_{j,o}^L[m,n],C_{j,o}^O[m,n],C_{j,o}^S[m,n],C_{j,o}^T[m,n]) \quad \text{(Equation 26)}$$

$C^{(4)}(\ldots)$ is a function, represented by $$C^{(4)}(C_{j,o}^L[m,n],C_{j,o}^O[m,n],C_{j,o}^S[m,n],C_{j,o}^T[m,n])=(C_{j,o}^L[m,n]+C_{j,o}^O[m,n]+C_{j,o}^S[m,n]+C_{j,o}^T[m,n])/4 \quad \text{(Equation 27)}$$

for instance.

Figure 14B:
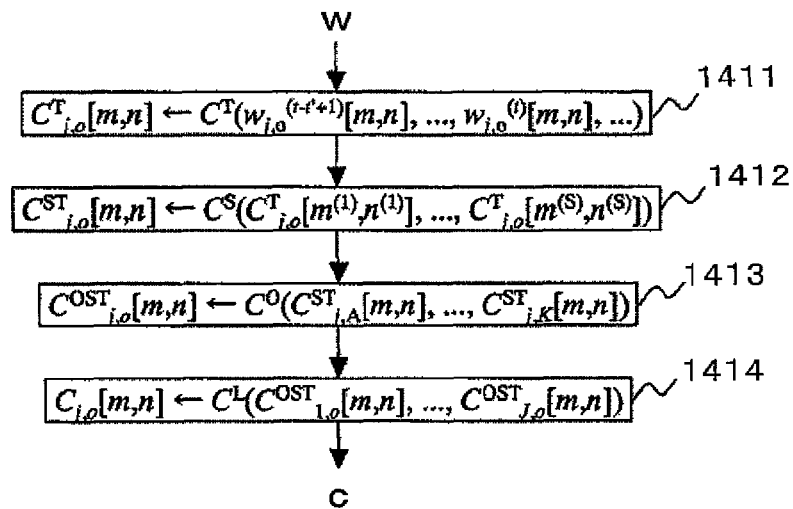

FIG. 14(b) charts conservation degree calculation in another exemplary embodiment. In the embodiment charted in FIG. 14(a), while the functions $C^L(\ldots)$, $C^O(\ldots)$, $C^S(\ldots)$ and $C^T(\ldots)$ are used in parallel, the functions $C^L(\ldots)$, $C^O(\ldots)$, $C^S(\ldots)$ and $C^T(\ldots)$ are used in series in the embodiment of FIG. 14(b) as in that of FIG. 11(b). First, the value $C^T$ is calculated in a block 1411 by a calculation method represented by (Equation 24) as a function of resolution coefficients $w_{j,o}^{(t-t'+1)}[m, n]$, $w_{j,o}^{(t-t'+2)}[m, n]$, ..., $w_{j,o}^{(t)}[m, n]$ of different frames at or in the same resolution level j, edge direction o and positions (m, n).

Next, the value $C^{ST}$ as represented by the following equation is calculated in a block 1412 by using the function $C^S(\ldots)$ like the one used in (Equation 15) from values $C_{j,o}^T[m^{(1)}, n^{(2)}]$, $C_{j,o}^T[m^{(S)}, n^{(S)}]$ at or in the same resolution level j and edge direction o in different positions.

$$C_{j,o}^{ST}[m,n]=C^S(m,n; C_{j,o}^T[m^{(1)},n^{(1)}],\ldots,C_{j,o}^T[m^{(S)},n^{(S)}]) \quad \text{(Equation 28)}$$

Similarly hereinafter, in blocks 1413 and 1414, the conservation degree C is calculated by performing the calculation represented by the following equations using functions $C^L(\ldots)$ and $C^O(\ldots)$ like those used in (Equation 11) and (Equation 13).

$$C_{j,o}^{OST}[m,n]=C^O(o;C_{j,A}^{ST}[m,n],\ldots,C_{j,K}^{ST}[m,n])$$

$$C_{j,o}[m,n]=C^L(j;C_{1,o}^{OST}[m,n],\ldots,C_{j,o}^{OST}[m,n]) \quad \text{(Equation 29)}$$

Incidentally, the functions are brought to work on the resolution coefficients w in the sequence of $C^T$, $C^S(\ldots)$, $C^O(\ldots)$ and $C^L(\ldots)$ in the embodiment charted in FIG. 14(b), this sequence is not the only possible choice. Further, as another embodiment not shown, a combination of processing in series and processing in parallel may as well be used as processing in the embodiment charted in FIG. 11(c).

Next, reconstruction processing will be described with reference to FIG. 15.

Figure 15A:
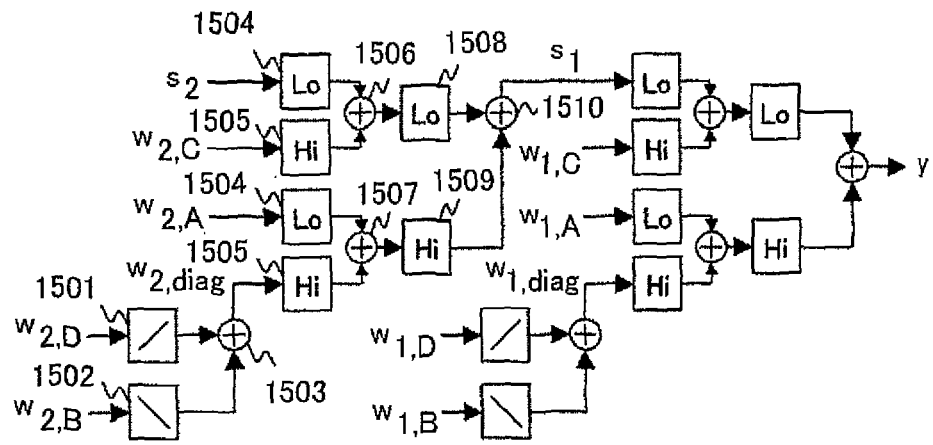
FIGS. 15(a)-(c) are block diagrams showing the method of reconstruction.
Figure 15B:
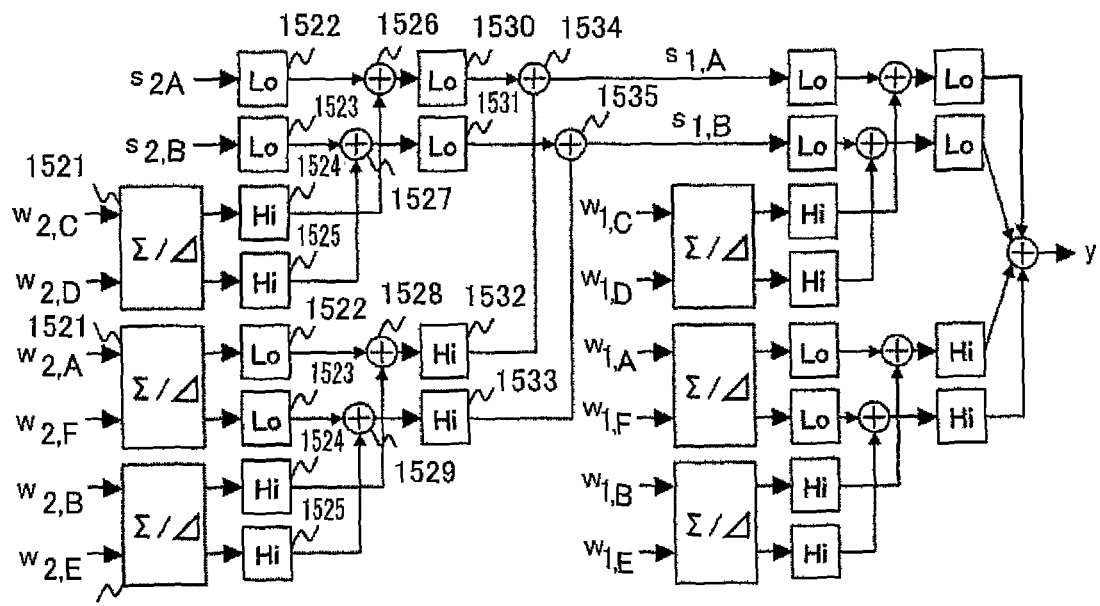
Figure 15C:
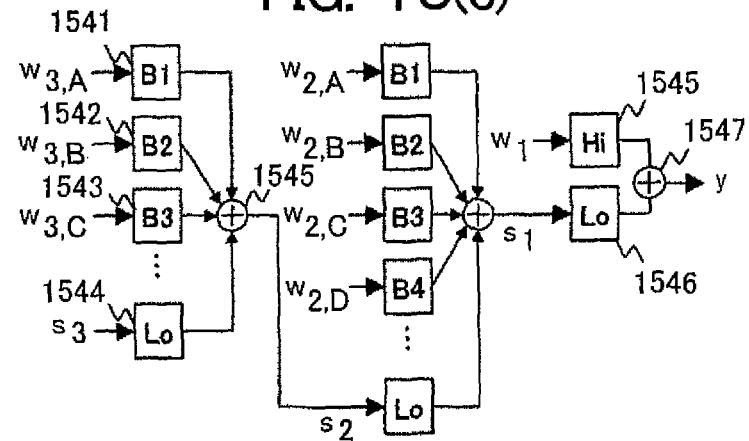

FIGS. 15(a), 15(b) and 15(c) illustrate exemplary embodiments of reconstruction processing flow respectively matching multi-level resolving systems based on Wavelet transform, complex Wavelet transform and steerable pyramid transform. They respectively correspond to processing flows of FIGS. 3(a), 3(b) and 3(c). The resolution coefficients s and w in FIG. 15 represent amplitude-corrected resolution coefficients.

First, the embodiment diagram representing the reconstruction processing flow in the case of Wavelet transform in FIG. 15(a) will be described. In this embodiment, reconstruction is processed in the reverse sequence of steps of multi-level resolution described with reference to FIG. 3(a). First, a filter 1501 that passes the edge parallel to the straight line m=n and cuts off the edge parallel to the straight line m=−n and a filter 1502 that, conversely, cuts off the edge parallel to the straight line m=n and passes the edge parallel to the straight line m=−n are applied to high frequency resolution coefficients $w_{J-1,B}$ and $w_{J-1,D}$, of a resolution level J-1 (J=3 in this embodiment), and then the sum $w_{J-1,diag}$ of outputs obtained from the filtering is calculated in a block 1503.

Next, after applying a vertical one-dimensional low-pass filter 1504 and a vertical one-dimensional high-pass filter 1505 to resolution coefficients $s_{J-1}$, $w_{J-1,C}$, $w_{J-1,A}$ and $w_{J-1,diag}$, the sum of the outputs of the filters is calculated in blocks 1506 and 1507. Then, a horizontal one-dimensional low-pass filter 1508 and high-pass filter 1509 are applied, and by calculating the sum of the results in a block 1510, a low frequency resolution coefficient $s_{J-2}$ of a resolution level J-2 is figured out.

As in the case of multi-level resolution, the coefficients of these filters are real numbers, and the sequence of applying the horizontal filters and the vertical filters may be reverse. Further, in the multi-level resolution processing described with reference to FIG. 3(a), if decimation is applied immediately after the filtering, a pixel of zero in brightness is inserted (hereinafter referred to as interpolation) after every other pixel immediately after the corresponding filtering in this exemplary embodiment. By recurrently repeating the same processing after this, a low frequency resolution coefficient $s_{j-1}$ of a resolution level j-1 is figured out from a resolution coefficient of a resolution level j. Finally, a quality-improved image y is obtained from a resolution coefficient of a resolution level 1 by applying processing similar to the foregoing.

Next, one exemplary embodiment of reconstruction processing flow in the case of complex Wavelet transform shown in FIG. 15(b) will be described.

In a reverse procedure to the steps of multi-level resolution described with reference to FIG. 3(b), first, high frequency resolution coefficients $w_{J1,A}$, $w_{J1,B}$, $w_{J1,C}$, $w_{J1,D}$, $w_{J1,E}$ and $w_{J1,F}$ of of a resolution level J-1 (J=3 in this embodiment) are subjected to processing to calculation the sum of and differences between input signals in a ΣΔ block 1521. Next, after applying vertical one-dimensional low-pass filters 1522, 1523 and vertical one-dimensional high-pass filters 1524, 1525 to the output signals of the ΣΔ block 1521 and low frequency resolution coefficients $s_{J-1,A}$ and $s_{J-1,B}$ of the resolution level J-1, the sum is calculated in blocks 1526, 1527, 1528 and 1529. Then, by calculating the sum in blocks 1534 and 1535 after applying horizontal one-dimensional low-pass filters 1530, 1531 and high-pass filters 1532, 1533, a low frequency resolution coefficients $s_{J-2,A}$ and $s_{J-2,B}$ of a resolution level J-2 are figured out.

Although filters of two different types each are used for each round of filtering in this illustration of the exemplary embodiment, this is not the only applicable combination. The coefficients of these filters are complex numbers. The sequence of applying the horizontal filters and vertical filters may as well be reversed.

Further, in the multi-level resolution processing described with reference to FIG. 3(*b*), if decimation is applied immediately after the filtering, interpolation is applied immediately before the corresponding filtering in this exemplary embodiment. By recurrently performing the same processing after this, low frequency resolution coefficients $s_{j-1}$ and $s_{j-2}$ of a resolution level j-1 is figured out from a resolution coefficient of a resolution level j. Finally, a quality-improved image y is obtained from a resolution coefficient of a resolution level 1 by applying processing similar to the foregoing.

Next, the embodiment diagram representing the reconstruction processing flow in the case of steerable pyramid transform of FIG. 15(*c*) will be described. In a reverse procedure to the steps of multi-level resolution described with reference to FIG. 3(*c*), first, filters 1541, 1542, 1543, . . . of high frequency in either the vertical or horizontal direction and passing components in a specific edge direction are applied to resolution coefficients $W_{J-1,A}$, $w_{J-1,B}$, $w_{J-1,C}$, . . . of a resolution level J-1 (J=3 in this embodiment). To the resolution coefficient $s_{J-1}$, a two-dimensional low-pass filter 1544 passing only low frequency components in both the vertical and horizontal directions is applied. Next, $s_{J-2}$ is figured out by calculating in a block 1545 the sum of the outputs of the filters 1541, 1542, 1543 and 1544.

In the multi-level resolution described with reference to FIG. 3(*c*), if decimation is applied immediately after the two-dimensional low-pass filtering, interpolation is applied immediately before the corresponding filtering in this exemplary embodiment. By recurrently performing the same processing after this, the low frequency resolution coefficient $s_{j-1}$ of the resolution level j-1 is figured out from the resolution coefficient of the resolution level j. Finally, by calculating in a block 1547 the sum of the signal obtained by applying a two-dimensional low-pass filter 1546 to $s_1$ and the signal obtained by applying to $w_1$ a two-dimensional high-pass filter 1545 which cuts off only those components that are low in frequency in both the vertical and horizontal directions, a quality-improved image y is obtained.

Next, image quality improvement that permits alteration of processing parameters according to imaging information will be described with reference to FIG. 16 and FIG. 17.

Figure 16:
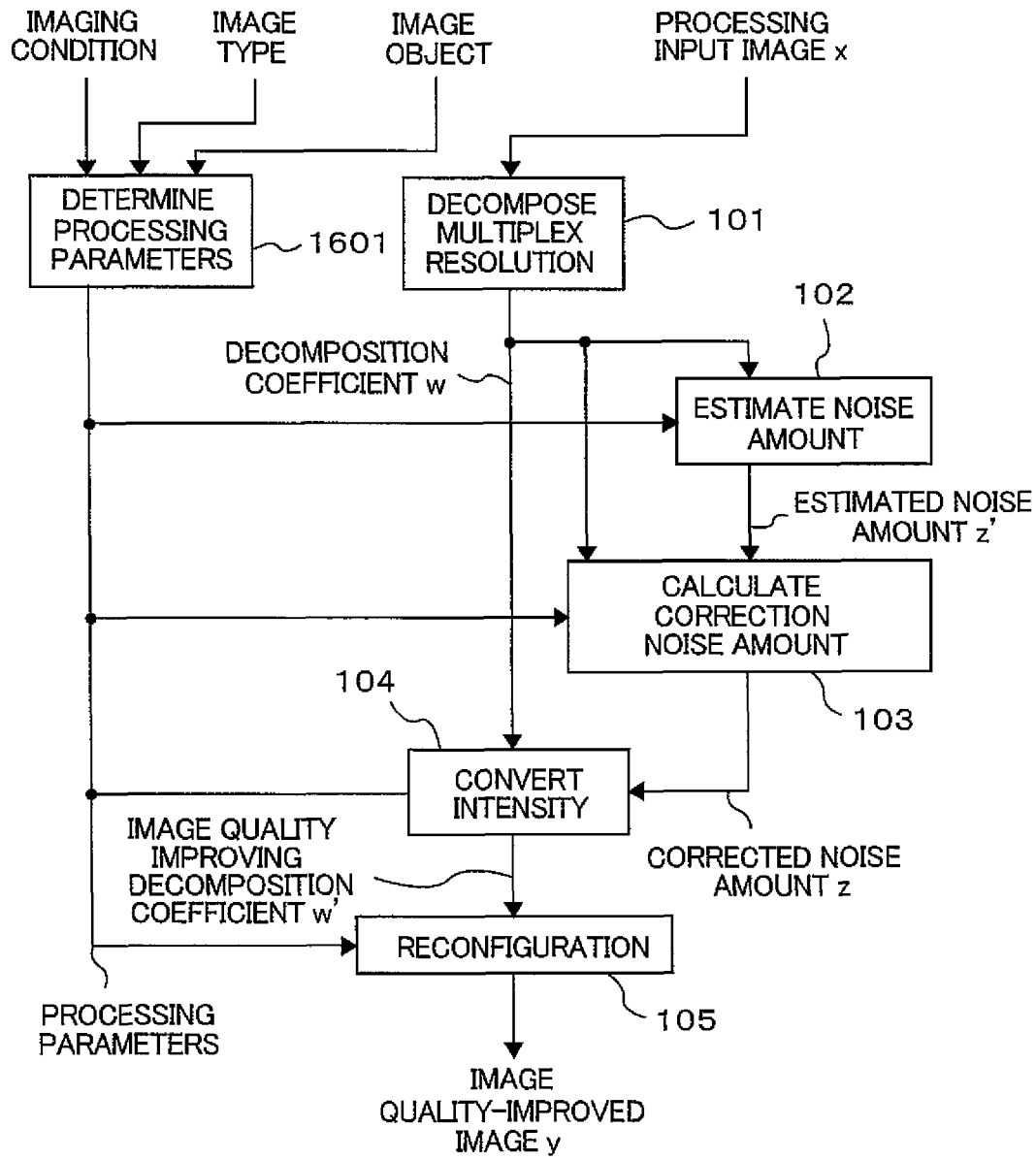
FIG. 16 is flow charts of image quality improvement permitting alterations of processing parameters according to the imaging conditions, the type of the image and the imaging object.

FIG. 16 is a diagram of an exemplary embodiment charting the flow of image quality improvement according to the invention. First, processing parameters are determined by processing parameter determination 1601 on the basis of the imaging conditions, the type of the image and the imaging object which constitute imaging information. A processing parameter for each item of imaging information is tabulated in advance. It is further possible to provide a function that allows the user to regulate values on the basis of processing parameters obtained from the table. Next, by using the determined processing parameters, the multi-level resolution processing 101, the noise amount estimation 102, the corrected noise amount calculation 103, the intensity conversion 104 and the reconstruction 105 are carried out. It has to be noted that a configuration in which multiple algorithms for performing different types of processing are made available in advance within each step or processing to permit switching over according to the processing parameters can also be used.

FIG. 17 shows an exemplary embodiment representing a table containing a processing parameter for each item of imaging information for use in the processing parameter determination 1601 of FIG. 16. The values in a table 1701 may be fixed in advance or a function to allow the user to alter the values may be provided as well. Each line in the table 1701 represents the processing parameter to be used for each item of imaging information.

The imaging information includes imaging conditions in column 1702, image type in column 1703 and imaging object in column 1704. More specifically, the information includes the type of ultrasound probe, magnification of display, frequency band in which ultrasound transmitted or received signals are used, whether spatial compounding is applied or not, whether frequency compounding is applied or not, and the scanning pitch of ultrasound transmitted signals. The processing parameters may further include parameters regarding multi-level resolution shown in column 1705, noise amount estimation in column 1706, corrected noise amount calculation, coefficient intensity conversion and reconstruction processing.

The table shall be of a form that uniquely determines the processing parameter for each item of imaging information. In this exemplary embodiment, the processing parameter stated on the topmost line out of the lines matching the pertinent item of imaging information in the table is applied.

Industrial Applicability

It is made possible to improve the image quality of ultrasound images, enhance the visibility of tissue structure and morbid regions and utilize such advantages in ultrasonographic devices.

Description of Reference Numerals

101: multi-level resolution; 102: noise amount estimation; 103: corrected noise amount calculation; 104: intensity conversion; 105: reconstruction; 201: ultrasonographic device; 202: drive circuit; 203: ultrasound probe; 204:receiver circuit; 205: image generator; 206: image quality improving unit; 207: multi-level resolution unit; 208: noise amount estimator; 209: noise amount corrector; 210: intensity converter; 211: reconstruction unit; 212: scan converter; 213: display; 221: input unit; 222: controller; 223: memory; 224: processor; 701: resolution coefficient amplitude conversion; 711: conservation degree calculation; 712: conservation degree-based resolution coefficient correction

The invention claimed is:

1. A method implemented by an image quality improving hardware processor, the method for improving an image from an ultrasonographic device and comprising:

figuring out, with the image quality improving hardware processor, a resolution coefficient of a generated image in each position from ultrasounds detected via an ultrasound probe of an ultrasonogaraphic device, by multi-level resolving to a plurality of resolutions, to obtain resolution coefficients for the plurality of resolutions, respectively;

estimating via calculation, with the image quality improving hardware processor, a noise amount for each resolution of the plurality of resolutions, on a basis of the resolution coefficients obtained from the figuring;

correcting, with the image quality improving hardware processor, the estimated noise amount for one or more resolution on a basis of a reliability of the estimated noise amount for the one or more resolution, where the reliability is calculated from one or more estimated noise amounts or resolution coefficients or a predetermined value;

converting, with the image quality improving hardware processor, the intensity of each of the resolution coefficients figured out, the converting using information on the corrected noise amount obtained from the correcting; and reconstructing, with the image quality improving hardware processor, an image by undergoing reconstruction processing to each of the resolution coefficients having undergone the intensity conversion from the converting.

2. The image quality improving method according to claim 1, wherein the converting carries out coefficient intensity conversion of each of the resolution coefficients by using values by which multiple resolution coefficients positioned in vicinities of the resolution coefficients have been subjected to weighted summing.

3. The image quality improving method according to claim 1, wherein the converting carries out coefficient intensity conversion of each of the resolution coefficients on a basis of the estimated noise amount and two or more resolution coefficients including resolution coefficients of a higher resolution level than the resolution level of the resolution coefficients.

4. The image quality improving method according to claim 1, wherein the converting carries out coefficient intensity conversion of each of the resolution coefficients by using resolution coefficients in a same position, at a same resolution level and in a same edge direction as picked-up images obtained at a different time from a time of acquisition of picked-up images to which the coefficient intensity conversion is applied.

5. The image quality improving method according to claim 1, wherein the converting carries out coefficient intensity conversion of each of the resolution coefficients by using values by which multiple resolution coefficients positioned in vicinities of the resolution coefficients have been subjected to weighted summing.

6. The image quality improving method according to claim 1, wherein the converting carries out coefficient intensity conversion of each of the resolution coefficients on a basis of the estimated noise amount and two or more resolution coefficients including resolution coefficients at a higher resolution level than a resolution level of the resolution coefficients.

7. The image quality improving method according to claim 1, wherein the converting carries out intensity conversion of each of the resolution coefficients by using resolution coefficients in a same position, at a same resolution level and in a same edge direction as picked-up images obtained at a different time from a time of acquisition of picked-up images to which the coefficient intensity conversion is applied.

8. An ultrasonographic device comprising:

an ultrasound probe structured to irradiate ultrasounds toward a subject and receive reflected waves from the subject; and a hardware processor configured to effect operations including:

figuring out a resolution coefficient of a generated image in each position from ultrasounds detected via the ultrasound probe, by multi-level resolving to a plurality of resolutions, to obtain resolution coefficients for the plurality of resolutions, respectively;

estimating, via calculation, a noise amount for each resolution of the plurality of resolutions, on a basis of the resolution coefficients obtained from the figuring;

correcting the estimated noise amount for one or more resolution on a basis of a reliability of the estimated noise amount for the one or more resolution, where the reliability is calculated from one or more estimated noise amounts or resolution coefficients or a predetermined value;

converting the intensity of each of the resolution coefficients figured out, the converting using information on the corrected noise amount obtained from the correcting; and reconstructing an image by undergoing reconstruction processing to each of the resolution coefficients having undergone the intensity conversion from the converting.

* * * * *